United States Patent
Ekholm et al.

(10) Patent No.: US 7,074,863 B2
(45) Date of Patent: *Jul. 11, 2006

(54) METALLOCENE CATALYSTS CONTAINING AN IDENYL MOIETY SUBSTITUTED AT THE 4,-5,-6- OR 7-POSITION BY A SILOXY OR GERMYLOXY GROUP

(75) Inventors: Peter Ekholm, Turku (FI); Hendrik Luttikhedde, Raisio (FI); Janne Maaranen, Kerava (FI); Antti Penninkangas, Kaarina (FI); Carl-Eric Wilen, Espoo (FI)

(73) Assignee: Borealis Technology Oy, Porvoo (FI)

( * ) Notice: Subject to any disclaimer, the term of this patent is extended or adjusted under 35 U.S.C. 154(b) by 30 days.

This patent is subject to a terminal disclaimer.

(21) Appl. No.: 10/481,332

(22) PCT Filed: Jun. 21, 2002

(86) PCT No.: PCT/GB02/02853

§ 371 (c)(1),
(2), (4) Date: Mar. 26, 2004

(87) PCT Pub. No.: WO03/000744

PCT Pub. Date: Jan. 3, 2003

(65) Prior Publication Data

US 2004/0152882 A1    Aug. 5, 2004

(30) Foreign Application Priority Data

Jun. 22, 2001  (GB) .................................. 0115370.9
Jul. 19, 2001  (GB) .................................. 0117629.6

(51) Int. Cl.
| | | |
|---|---|---|
| C08F 4/60 | (2006.01) | |
| C08F 4/64 | (2006.01) | |
| C08F 10/00 | (2006.01) | |
| C07F 7/18 | (2006.01) | |
| C07F 17/00 | (2006.01) | |

(52) U.S. Cl. .................. 526/126; 526/160; 526/161; 526/165; 526/172; 526/943; 502/152; 502/158; 556/410; 556/482

(58) Field of Classification Search ................ 502/152, 502/158; 526/126, 172, 160, 161, 165, 943; 556/410, 482

See application file for complete search history.

(56) References Cited

U.S. PATENT DOCUMENTS

| | | |
|---|---|---|
| 5,304,614 A | 4/1994 | Winter et al. |
| 5,483,002 A | 1/1996 | Seelert et al. |
| 5,504,232 A | 4/1996 | Winter et al. |
| 5,672,668 A | 9/1997 | Winter et al. |
| 6,160,184 A | 12/2000 | McMorris |

FOREIGN PATENT DOCUMENTS

| | | |
|---|---|---|
| EP | 0 705 281 B1 | 3/1998 |
| WO | 93/11258 A | 6/1993 |
| WO | WO 93/11258 | 6/1993 |
| WO | WO 94/28034 | 12/1994 |
| WO | WO 96/00243 | 1/1996 |
| WO | WO 96/32423 | 10/1996 |
| WO | WO 96/38458 | 12/1996 |
| WO | WO 97/28170 | 8/1997 |
| WO | WO 98/46616 | 10/1998 |

OTHER PUBLICATIONS

Linnolahti et al, "Theoretical Study on the Factors Controlling the Accessibility of Cationic Metal Centers in Zirconocene Polymerization Catalysts", Macromolecules 2000, 33, 9205-9214; XP-002187589.

Luttikhedde et al, "Bis(triisopropylsiloxyindenyl) zirconocenes", Journal of Organometallic Chemistry, 555 (1998) 127-134.

Tanaka et al, "Synthetic Studies on a Picrotoxane Sesquiterpene, Coriamyrtin. II.[1]) An Effective Stereocontrolled Synthesis of the Picrotoxane Skeleton Except for a $C_1$ Unit at the $C_9$ Position and Functionalziation of the Five-Membered Ring", Chem. Pharm. Bull. 31(6)1958-1971(1983); XP-001108954.

Leino et al, "Isospecific Propylene Polymerization with a Novel 2-Substituted Bis(indeny) ansa-Zirconocene", Organometallics 1996, 15, 2450-2453.

Leino et al, "Homogeneous α-Olefin Polymerizations over Racemic Ethylene-Bridged ansa-Bis(2-tert-butyldimethylsiloxy)-1-indenyl) and ansa-Bis(2-tert-butyldimethylsiloxy)-4,5,6,7-tetrahydro-1-indenyl) Metallocene Dichlorides", Macromolecules 1997, 30, 3477-3483.

Linnolahti et al; "Theoretical Study on the Factors Controlling the Accessibility of Cationic Metal Centers in Zirconocene Polymerization Catalysts"; 2000, 33 (25), 92-0-9214, XP002187589.

Luttikhedde et al; "Bis(Triisopropylsiloxyindenyl) Zirconocenes"; Journal of Organometallic Chemistry, Elsevier-Sequoia S.A. Lausanne, CH, vol. 555, No. 1, Mar. 25, 1998, pp. 127-134, XP004128622.

Tanaka et al; "Synthetic Studies on a Picrotoxane Sesquiterpene, Coriamyrtin. II. An Effective Stereocontrolled Synthesis of the Picrotoxane Skeleton Except for a C1 Unit at the C9 Position and Functionalization of the Five-Membered Ring"; Chem. Pharm. Bull., 1983, 31(6), 1958-71 XP001108954.

*Primary Examiner*—Caixia Lu
(74) *Attorney, Agent, or Firm*—Nixon & Vanderhye P.C.

(57) ABSTRACT

A metallocene catalyst in which the metal is coordinated by a η5 cyclopentadienyl ligand which forms part of an indenyl or indenyloid moiety, characterized in that said moiety is directly or indirectly substituted at the 4-, 5-, 6- or 7-position by a pendant siloxy or germyloxy group.

26 Claims, No Drawings

METALLOCENE CATALYSTS CONTAINING AN IDENYL MOIETY SUBSTITUTED AT THE 4,-5,-6- OR 7-POSITION BY A SILOXY OR GERMYLOXY GROUP

This application is the US national phase of international application PCT/GB02/02853, filed in English on 21 Jun. 2002, which designated the US. PCT/GB02/02853 claims priority to GB Application No. 0115370.9, filed 22 Jun. 2001 and GB Application No. 0117629.6, filed 19 Jul. 2001. The entire contents of these applications are incorporated herein by reference.

This invention relates to catalysts for olefin polymerisation, in particular to catalysts which comprise a metal bonded to a pentahapto ($\eta^5$) cyclopentadienyl moiety, fused to at least one 6-membered ring.

In olefin polymerizations, it has long been known to use as a catalyst system the combination of a metallocene procatalyst and an alumoxane co-catalyst or catalyst activator.

By "metallocene" is meant here a metal complex which comprises at least one ligand complexed to a metal and having a hapticity of 2 or greater, for example 2 to 5, especially 5. Metallocenes which comprise one or more pentahapto ($\eta^5$) ligands, for example the cyclopentadienyl ligand, have assumed greatest importance and the subsequent discussion will focus mainly on but is not limited to this subtype of multihapto-containing metal-ligand complexes.

The metallocene may for example be a so-called "open sandwich" or "half sandwich" compound in which the metal is complexed by a single multihapto $\eta^5$ ligand; a "sandwich" compound in which the metal is complexed by 2 or more such ligands; a "handcuff compound" in which the metal is complexed by a bridged bis-multihapto ligand, for example a bis-$\eta^5$-ligand; or a "scorpionate compound" in which the metal is complexed by a multihapto (e.g. $\eta^5$) ligand bridged to a $\eta^1$ (for example a σ-bonded) ligand.

Metallocenes have been much used in the copolymerization of olefins, especially ethylene, propylene, other α-olefins and higher olefins, in the presence of a co-catalyst/catalyst activator such as an alumoxane.

Alumoxanes are compounds with alternating aluminium and oxygen atoms, generally compounds of formula I or II

(I)

(II)

where each R, which may be the same or different, is a $C_{1-10}$ alkyl group, and p is an integer having a value between 0 and 40). These compounds may be prepared by reaction of an aluminium alkyl with water. The production and use of alumoxanes is described in the patent literature, especially the patent applications of Texas Alkyls, Albemarle, Ethyl, Phillips, Akzo Nobel, Exxon, Idemitsu Kosan, Witco, BASF and Mitsui.

Traditionally, the most widely used alumoxane is methylalumoxane (MAO), an alumoxane compound in which the R groups are methyl groups. MAO however is poorly characterised, appears to comprise a range of cage-like structures more complex than the simple linear or cyclic structures of formulae I and II, and is relatively expensive.

Accordingly, efforts have been made to use alumoxanes other than MAO. Thus, for example WO98/32775 (Borealis) proposes the use of metallocene procatalysts with alumoxanes in which R is a $C_{2-10}$ alkyl group, e.g. hexaisobutylalumoxane (HIBAO).

The contents of WO98/32775 and all other publications referred to hereafter are hereby incorporated by reference.

Much effort has been expended into the development of improved metallocene-containing catalyst systems on account of the economic importance of olefin polymers. Of particular relevance are the investigations into indenyl-containing metallocenes in which the 5-membered cyclopentadienyl ring bonds in a $\eta^5$ fashion to the metal in the complex. For example WO 97/28170 (Borealis) discloses investigations into the substitution of the 5-membered ring of the indenyl moiety with alkoxy, siloxy and other groups. U.S. Pat. Nos. 5,672,668, 5,504,232 and 5,304,613 (all to Winter et al.) disclose, inter alia, handcuff compounds or other metallocenes comprised of indenyl-based complexes, particularly those in which the 6-membered ring in the indenyl moiety is functionalised with one or more hydrocarbyl or halohydrocarbyl substituents.

U.S. Pat. No. 5,483,002 (to Seelert et al.) discloses similar types of bis indenyl-based metallocenes. Exemplary of such 5,6 fused systems is the indenyl system.

Chiral $C_2$-symmetric bis(indenyl) ansa-metallocenes are precursors to highly active catalysts for stereoselective polymerisation of alpha-olefins. The performance characteristics of these systems are different, the variations being induced by size and position of the substituents. For example, dimethylsilylene bridged 2,2'-dimethyl-4,4'-diaryl substituted bis(indenyl) zirconocenes developed by Brintzinger and co-workers (*Organometallics* 1994, 13, 964) and Spaleck et al. (*Organometallics* 1994, 13, 954), catalyse the production of isotactic polypropylenes with catalyst activities and polymer properties comparable to those obtained with heterogeneous Ziegler-Natta catalysts.

Research into electronically altered indenyl and bis(indenyl) metallocenes, however, has remained relatively sparse. So too are reports of electronically modified indenyloid and bis(indenyloid) ligands. As used herein, the term indenyloid is intended to embrace the general class of anions formed by the deprotonation of any 5,6-fused system whereby to form a cyclopentadienyl $\eta^5$ ligand fused to a 6-membered ring. Indenyl itself may be considered as the parent indenyloid but will be referred to as indenyl here. The fluorenyl ligand is an example of an indenyloid ligand.

Previously, it has been reported that halogen or alkoxy substitution in the six-membered rings of indenes reduces the activity of the catalyst system and the molecular weight of the produced polymer (Consiglio et al., *Organometallics* 1990, 9, 3098; Collins et al., *Organometallics* 1992, 11, 2115). Bis(indenyl) zirconocenes with 2-amino functionalised ligands have been reported by several groups (Luttikhedde et al., *Organometallics* 1996, 15, 3092; Plenio and Burth, *J. Organomet. Chem.* 1996, 519, 269; Brintzinger et al., *J. Organomet. Chem.* 1996, 520, 63). The bridged complexes show somewhat lower catalytic activities compared with their unsubstituted bis(indenyl) zirconocene analogues.

WO 97/28170 (supra) does in some way address this neglected area. However, this publication addresses the issue of electronically modifying, by way of substitution, the 5-membered ring of indenyl and indenyloid compounds whereby to produce metallocene compounds in which an oxygen atom is directly bonded to the 2-position of a $\eta^5$ indenyl moiety.

However, there have been no reports of metallocenes in which the 6-membered ring of an indenyl or indenyloid ring has been electronically modified by substitution by a pendant heteroatom attached group at the 4- or 7-position (i.e. a position adjacent to an atom participating in both the 5- and 6-membered rings).

Surprisingly, however, it has been found that a number of such compounds, viz metallocenes coordinated by a $\eta^5$ indenyl or indenyloid moiety in which a 6-membered ring fused directly or indirectly to the 5-membered ring is substituted by a siloxy or germyloxy group, exhibit advantageous properties. These complexes, when used as procatalysts in α-olefin polymerisation, allow the production of α-olefin homo or copolymers with notably higher molecular weight than achievable with analogous compounds in which the 6-membered ring is not substituted by a siloxy or germyloxy group. Moreover the activity of these complexes in polymerisations is high, as measured by the quantity of polymer produced per unit time against the quantity of metallocene used; and in copolymerisations, the complexes of the invention result in higher comonomer incorporation than do analogous compounds in which the 6-membered ring is not substituted by a siloxy or germyloxy group.

Viewed from one aspect, therefore the present invention provides a metallocene catalyst in which the metal is coordinated by a $\eta^5$ cyclopentadienyl ligand which forms part of an indenyl or indenyloid moiety, characterised in that said moiety is directly or indirectly substituted at the 4- 5-, 6- or 7-position, preferably the 4- or 7-position, by a pendant siloxy or germyloxy group.

As used herein the term metallocene catalyst is intended to embrace the actual catalytic species. This may be the metallocene compound itself or a metallocene procatalyst by which term is meant a compound which may be brought into a catalytically active state (e.g. for catalysis of α-olefin polymerization) by reaction with a co-catalyst or catalyst activator, e.g. an aluminium alkyl or other aluminium compound or a boron compound.

The metal will generally be a transition metal or lanthanide, especially a Group 3 (i.e. including scandium) to Group 7 (i.e. including manganese) transition metal, particularly a Group 4 to 6 metal, in particular Zr, Ti or Hf. For the avoidance of doubt, lanthanide metals herein include lanthanum itself.

Viewed from a further aspect, the invention provides an olefin polymerisation catalyst system comprising or produced by the reaction of:

(i) a metallocene catalyst in which the metal is coordinated by a $\eta^5$ cyclopentadienyl ligand which forms part of an indenyl or indenyloid moiety, characterized in that said moiety is directly or indirectly substituted at the 4- 5-, 6- or 7-position by a pendant siloxy or germyloxy group; and (ii) a cocatalyst/catalyst activator, e.g. an aluminium alkyl compound, in particular an alumoxane, especially an aluminum alkyl compound comprising alkyl groups containing from 1 to 6 carbon atoms.

Alternatively, said aluminum alkyl compound may be one which contains at least two carbon atoms.

Viewed from a still further aspect, the invention provides a process for olefin polymerisation comprising polymerising an olefin in the presence of a metallocene catalyst in which the metal is coordinated by a $\eta^5$ cyclopentadienyl ligand which forms part of an indenyl or indenyloid moiety, characterised in that said moiety is directly or indirectly substituted at the 4- 5-, 6- or 7-position by a pendant siloxy or germyloxy group.

Viewed from a yet another aspect, the invention provides a process for the preparation of a metallocene catalyst which comprises metallating a $\eta^5$ cyclopentadienyl ligand which forms part of an indenyl or indenyloid moiety with a transition metal or lanthanide, characterised in that said moiety is directly or indirectly substituted at the 4- 5-, 6- or 7-position by a pendant siloxy or germyloxy group.

Alternatively, it will be understood that the metallocene catalyst may be produced by the exchange of a metal ion in an existing metallocene for another metal ion through transmetallation.

Viewed from a different aspect, the invention provides an olefin polymer produced in a polymerisation process catalysed by an olefin polymerisation catalyst system comprising or produced by the reaction of (i) a metallocene catalyst in which the metal is coordinated by a $\eta^5$ cyclopentadienyl ligand which forms part of an indenyl or indenyloid moiety, characterised in that said moiety is directly or indirectly substituted at the 4- 5-, 6- or 7-position by a pendant siloxy or germyloxy group; and (ii) a cocatalyst/catalyst initiator, e.g. an aluminium alkyl compound, in particular an alumoxane, especially an aluminum alkyl compound comprising alkyl groups containing from 1 to 6 carbon atoms.

Alternatively, said aluminum alkyl compound may be one which contains at least two carbon atoms.

Viewed from an alternative aspect, the invention provides the use in olefin polymerisation of a metallocene catalyst in which the metal is coordinated by a $\eta^5$ cyclopentadienyl ligand which forms part of an indenyl or indenyloid moiety, characterised in that said moiety is directly or indirectly substituted at the 4- 5-, 6- or 7-position by a pendant siloxy or germyloxy group.

By directly or indirectly is meant that the pendant siloxy or germyloxy group is either directly bonded to one of the carbon atoms at position 4, 5, 6 or 7 (throughout this specification the numbering of carbon atoms is derived from the IUPAC numbering scheme for the indenyl ring) or is attached to one of these atoms, for example, by way of one or more intervening atoms, which may form a fused ring.

For the avoidance of doubt, however, the invention does not relate to metallocene catalysts containing only $\eta^5$ cyclopentadienyl ligands which form part of an indenyl or indenyloid moiety which contain only one or more directly bonded siloxy or germyloxy substituents at the 1-, 2- or 3- positions and no other siloxy or germyloxy substituents elsewhere.

Thus the catalyst of the invention may for example be a compound of formula (III):

$$(Lig)_pM(X)_m(A)_n \qquad \qquad (III)$$

in which:

M is a transition metal ion or a lanthanide metal ion;

p is 1 or 2;

m is greater than or equal to 0;

n is greater than or equal to 0;

n+m is equal to the valency of the metal not satisfied by ligand or ligands Lig;

X is a ligand which co-ordinates to M (for example a $\eta^5$ hydrocarbyl, $\eta^1$ hydrocarbyl, halo, hydrocarbyl amino or hydrocarbyl amido ligand);

A is a σ-ligand as defined hereinafter; and each ligand Lig which may be the same or different is a $\eta^5$ cyclopentadienyl ligand which forms part of an indenyl or indenyloid moiety, characterised in that said moiety is directly or indirectly substituted at the 4- 5-, 6- or 7-position by a pendant siloxy or germyloxy group, for example (Lig)$_p$ may be one or two of ligands In as defined hereafter.

M in the metallocene catalysts of the invention is preferably a group 4 to 6 transition metal, e.g. a metal selected from Ti, Zr, Hf, V, Nb, Ta, Cr, Mo and W. However, the metal is preferably Cr, Ti, Zr or Hf, particularly Cr if M is liganded by a single multihapto group or Ti, Zr or Hf if M is η-liganded by one or more multihapto groups.

Useful indenyl or indenyloid ligands according to the invention may be represented by symbol "In" wherein In consists of a negatively charged indenyl or indenyloid moiety of the following formula (IV):

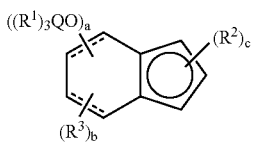

(IV)

wherein one or more of the ring carbon atoms may be replaced by a ring heteroatom;

each Q is either a silicon or a germanium atom;

either or both of the bonds shown as ----- may be present or absent;

each $R^1$ which may be the same or different is a hydrogen or a $C_{1-20}$ hydrocarbyl especially an alkenyl or alkyl group, especially a $C_{1-8}$ group, or a $\eta^1$ ligand (for example a σ ligand such as a nitrogen-containing group such as amine, at least one $R^1$ being other than hydrogen;

each $R^2$ may be hydrogen or a group bonded to the 5-membered ring through an atom of groups 14, 15 ot 16 of the periodic table (IUPAC) carbon, oxygen, silicon, germanium, nitrogen or sulfur, e.g. $C_{1-20}$ hydrocarbyl, hydrocarbyl siloxy, hydrocarbyloxy, hydrocarbylgermyloxy, hydrocarbyl silyl or hydrocarbylgermyl group particularly an oxygen-, silicon-, germanium- or sulfur-attached hydrocarbyl group;

each $R^3$ may be hydrogen or a group bonded to the 6-membered ring through an atom of groups 14, 15 ot 16 of the periodic table (IUPAC) carbon, oxygen, silicon, germanium, nitrogen or sulfur, e.g. $C_{1-20}$ hydrocarbyl, hydrocarbyl siloxy, hydrocarbyloxy, hydrocarbylgermyloxy, hydrocarbyl silyl or hydrocarbylgermyl group particularly an oxygen-, silicon-, germanium- or sulfur-attached hydrocarbyl group; or two or more $R^2$ and/or two or more $R^3$ groups attached to adjacent ring atoms on the same ring together form a 5- to 8-membered fused ring; and optionally one $R^2$ or $R^3$ is —L—Z wherein L is a 1 to 4 atom chain and Z is a second moiety, which may the same as or different to said first moiety, preferably of formula (IV) and joined to L through one $R^2$ or $R^3$, if present in which L is one and the same chain common to both moieties, a is an integer between 1 and 3, b is an integer between 1 and 3, the sum of a and b being no more than 4, c is an integer between 1 and 3, with the proviso that no more than one —L—Z group is present in each ligand In.

Preferably L—Z where present is attached to the 5-membered ring, especially at the 1- or 3-positions or less preferably to the 6-membered ring at the 4- or 7 positions.

The ligands in themselves are novel and form a further aspect of the invention. Viewed from this aspect, therefore, there is provided a ligand of formula (IV)

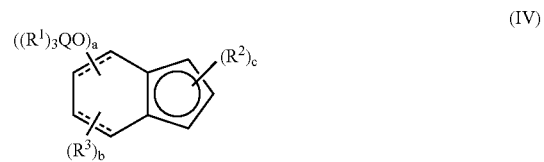

(IV)

(wherein one or more of the ring carbon atoms may be replaced by a ring heteroatom;

each Q is either a silicon or a germanium atom;

either or both of the bonds shown as ----- may be present or absent;

each $R^1$ which may be the same or different is a hydrogen or a $C_{1-20}$ hydrocarbyl especially an alkenyl or alkyl group, especially a $C_{1-8}$ group, or a $\eta^1$ ligand (for example a σ ligand such as a nitrogen-containing group such as amine, at least one $R^1$ being other than hydrogen;

each $R^2$ may be hydrogen or a group bonded to the 5-membered ring through an atom of groups 14, 15 ot 16 of the periodic table (IUPAC) carbon, oxygen, silicon, germanium, nitrogen or sulfur, e.g. $C_{1-20}$ hydrocarbyl, hydrocarbyl siloxy, hydrocarbyloxy, hydrocarbylgermyloxy, hydrocarbyl silyl or hydrocarbylgermyl group particularly an oxygen-, silicon-, germanium- or sulfur-attached hydrocarbyl group;

each $R^3$ may be hydrogen or a group bonded to the 6-membered ring through an atom of groups 14, 15 ot 16 of the periodic table (IUPAC) carbon, oxygen, silicon, germanium, nitrogen or sulfur, e.g. $C_{1-20}$ hydrocarbyl, hydrocarbyl siloxy, hydrocarbyloxy, hydrocarbylgermyloxy, hydrocarbyl silyl or hydrocarbylgermyl group particularly an oxygen-, silicon-, germanium- or sulfur-attached hydrocarbyl group; or two or more $R^2$ and/or two or more $R^3$ groups attached to adjacent ring atoms on the same ring together form a 5- to 8-membered fused ring; and optionally one $R^2$ or $R^3$ is —L—Z wherein L is a 1 to 4 atom chain and Z is a second moiety, which may the same as or different to said first moiety, preferably of formula (IV) and joined to L through one $R^2$ or $R^3$, if present in which L is one and the same chain common to both moieties, a is an integer between 1 and 3, b is an integer between 1 and 3, the sum of a and b being no more than 4, c is an integer between 1 and 3, with the proviso that no more than one —L—Z group is present in each ligand In) and salts and complexes thereof.

For the avoidance of doubt, ligands In include homocyclic or heterocyclic indenyl/indenyloid moieties which may be optionally fused to other rings.

By fused or non-fused is meant that the indenyl or indenyloid ligand may have two carbon or heteroatoms also forming part of an additional ring which may itself by fused or an optionally substituted carbocyclic or heterocyclic ring etc. For example the fluorenyl ring is embraced by this invention.

By homo- or heterocyclic is meant that any ring of the indenyl ligand or indenyloid ligand may have only carbon ring atoms (i.e. homo or isocyclic) or may have ring atoms other than carbon (heterocyclic). Such ring heteroatoms may for example be, independently from each other, N, S, Se, O, P, B or Si.

The variables a, b and c are all preferably 1 or 2, espcially 1.

Preferred ligands In are those in which at least one group of formula —OQ(R¹)₃ is a siloxy or germyloxy group directly attached to the 4-position or the 7-position or indirectly attached to the 4-, 5-, 6- or 7-position. Also preferred are ligands In in which one or more of said moiety or moieties of formula (IV) contain 2 groups of formula (R¹)₃QO—, for example one such group at position 4 and one at position 7 in the indenyl or indenyloid ring.

In one embodiment, one of the groups R¹ is an amine, e.g. alkylamine, bound to the Si or Ge atom via a carbon atom of said amine, wherein the nitrogen atom acts as a σ-ligand coordinating any metal ion present. In such an embodiment it is preferred if L—Z is absent.

Especially preferably ligands of In are those in which one group R² is of formula —L—Z. Particularly preferred are those in which —L—Z is present at the 1-position and/or in which Z is another moiety of formula (IV), preferably attached to L through an R² group.

In ligands In, including those preferred types as described herein, L is preferably of formula (C(R²)₂)$_q$ or Si(R²)₂ in which q is one or 2 or more and R² is as hereinbefore defined but may not represent a group L—Z) but is preferably hydrogen or a hydrocarbyl group.

Compounds of formula (III) are preferably of formula (Lig)₂M(A)$_n$ wherein M, A and n are as hereinbefore defined; and (Lig)₂ is a ligand In in which one group R² in said first moiety of formula (IV) is —L—Z, where L is preferably of formula (CR²)₂, ((CR²)₂)₂ or Si(R²)₂ in which R² is as hereinbefore defined but is preferably hydrogen or a hydrocarbyl group and Z is a second moiety preferably of formula (IV) which may or may not be the same as the first moiety of formula (IV) with the proviso that L is attached to the 1-position in said second moiety of formula (IV).

Preferably, in the moiety or moieties of formula (IV) of ligands In there is no other substitution other than the substituents OQ(R¹)₃ and R²; i.e. R³=H.

Particularly preferred ligands In used according to the various aspects of the present invention are those of formula (V)

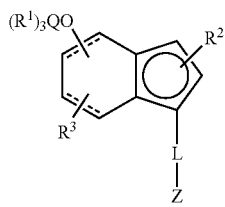

(V)

(wherein R¹, R², R³, Q and L—Z are as hereinbefore defined).

Preferably in ligands In, L is preferably of formula (C(R²)₂)₂ or Si(R²)₂ in which R² is as hereinbefore defined (but is not L—Z) and is preferably hydrogen or a hydrocarbyl group, for example methyl.

Examples of suitable (R¹)₃QO groups wherein Q=Si in the metallocene procatalysts of the invention include:

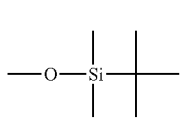 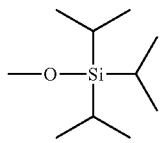

-continued

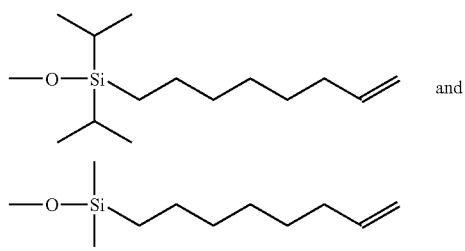

and

Thus typical examples of ligands of formula In include mono or bisanions of the following mono and bridged bis indenes:

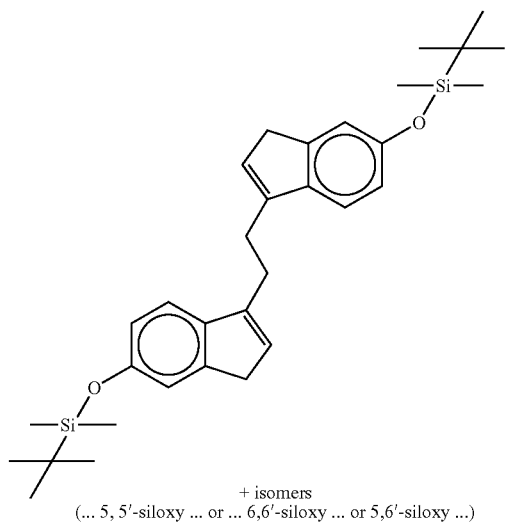

+ isomers
(... 5, 5'-siloxy ... or ... 6,6'-siloxy ... or 5,6'-siloxy ...)

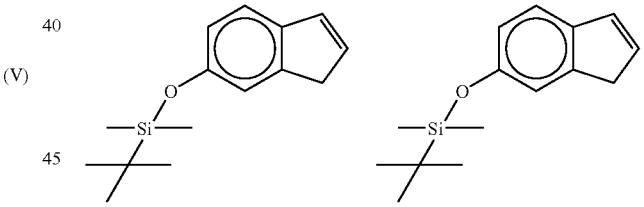

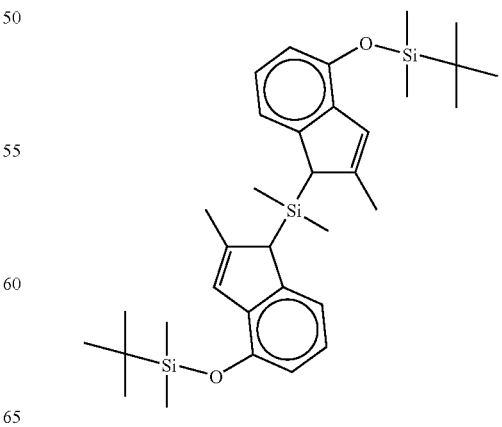

-continued
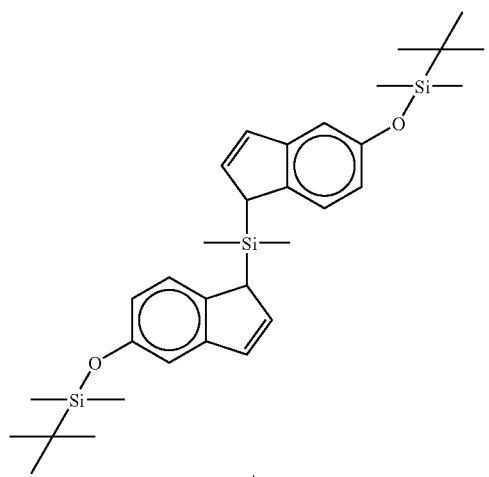
+ isomers
(... 5, 5'-siloxy ... or ... 6,6'-siloxy ... or 5,6'-siloxy ...)
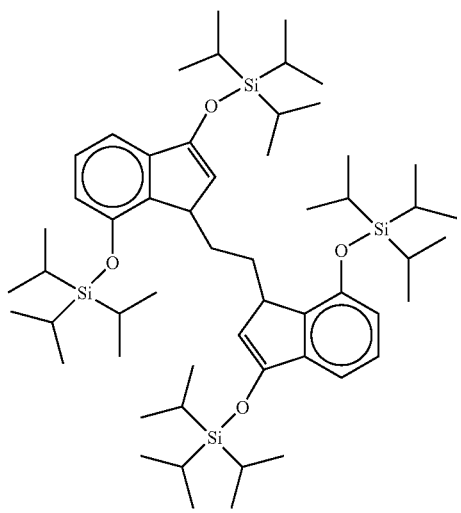
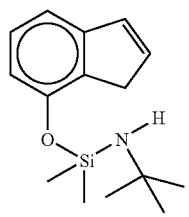 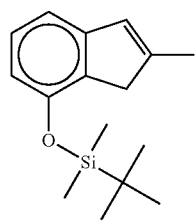
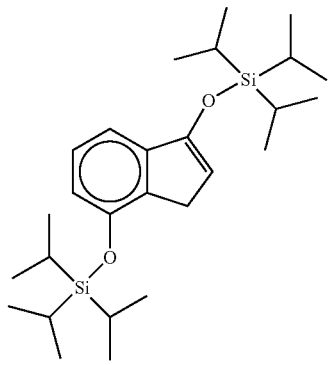
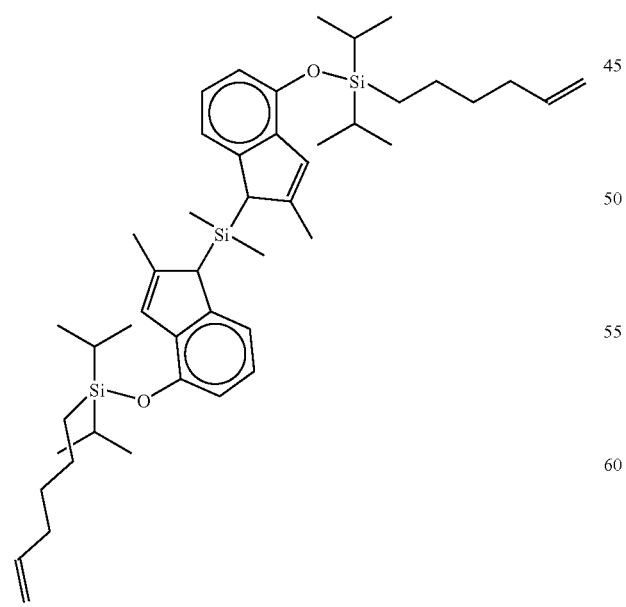
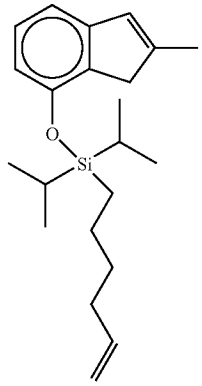

-continued
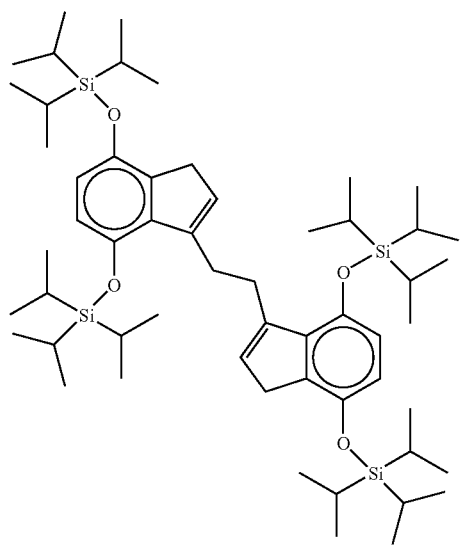
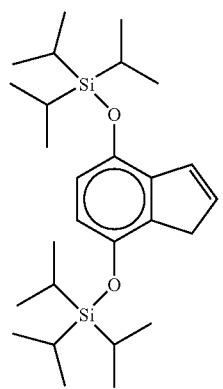
Typical examples of the metallocene catalysts of the invention thus include:
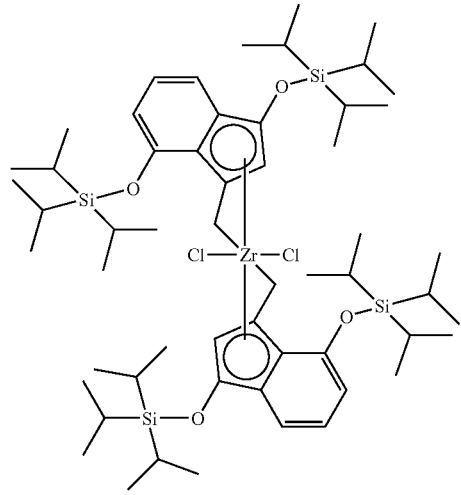
rac/meso
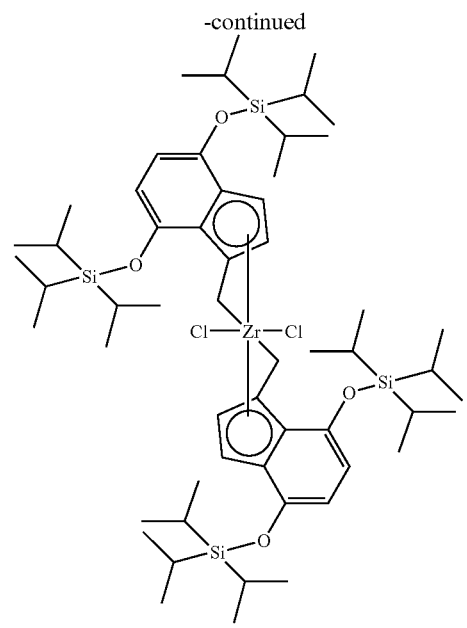
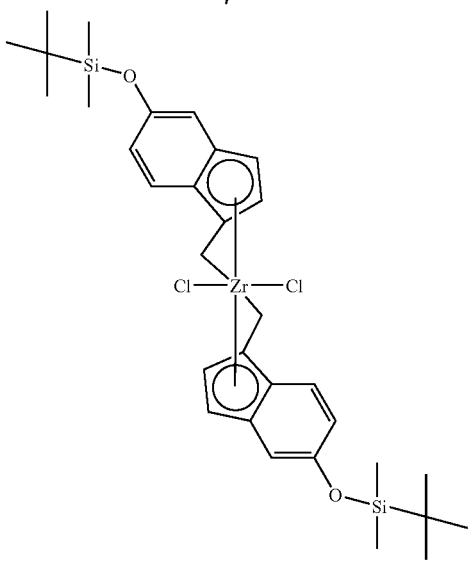
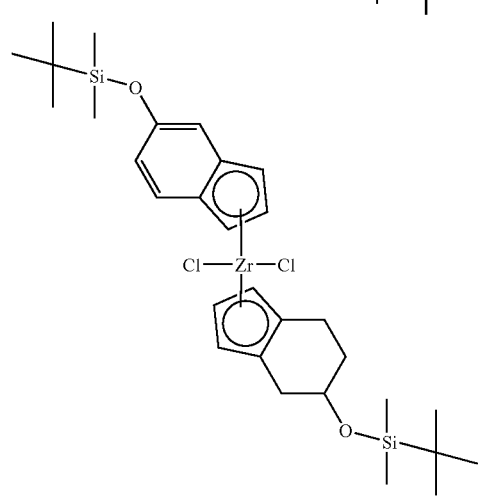
rac-like/meso-like -continued

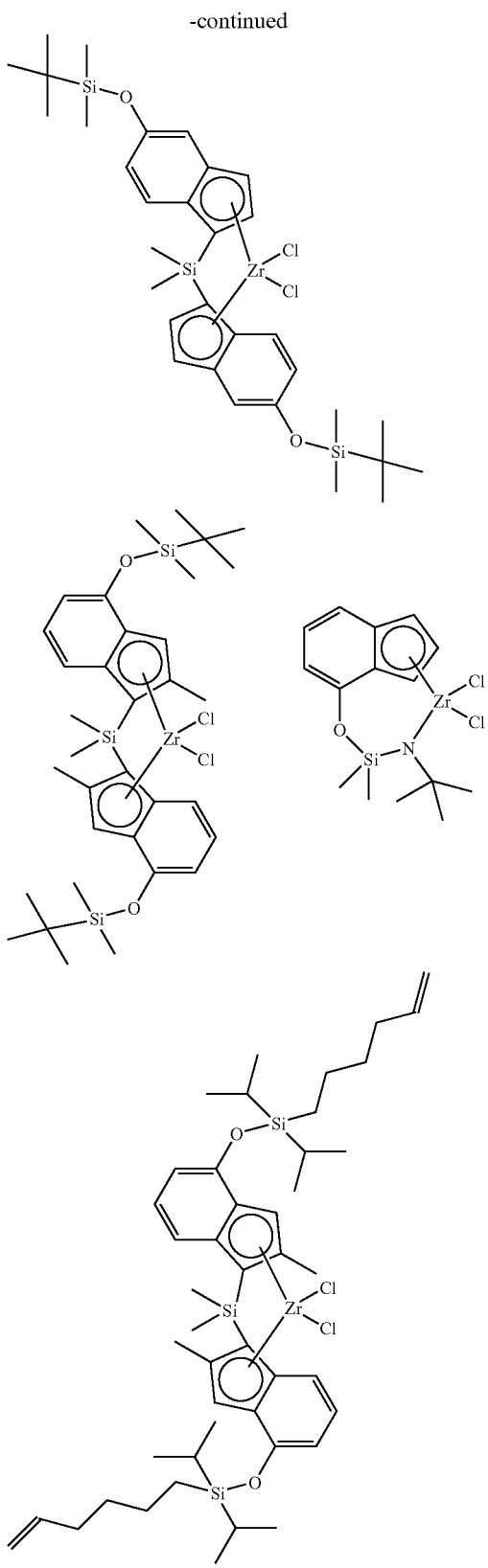

Examples of particular further η-ligands are well known from the technical and patent literature relating to metallocene olefin polymerization catalysts, e.g. EP-A-35242 (BASF), EP-A-129368 (Exxon), EP-A-206794 (Exxon), WO 97/28170 (Borealis), EP-A-318048, EP-A-643084, EP-A-69951, EP-A-410734, EP-A-128045, EP-B-35242 (BASF), EP-B-129368 (Exxon) and EP-B-206794 (Exxon).

These include
cyclopentadienyl,
indenyl,
fluorenyl,
octahydrofluorenyl,
methylcyclopentadienyl,
1,2-dimethylcyclopentadienyl,
pentamethylcyclopentadienyl,
pentyl-cyclopentadienyl,
2-dimethyl,tertbutylsiloxy-inden-1-yl,
n-butylcyclopentadienyl,
1,3-dimethylcyclopentadienyl,
4,7-dimethylindenyl,
1,-ethyl-2-methylcyclopentadienyl,
tetrahydroindenyl, and
methoxycyclopentadienyl.

By a σ-ligand moiety is meant a group bonded to the metal at one or more places via a single atom, eg a hydrogen, halogen, silicon, carbon, oxygen, sulphur or nitrogen atom. Examples of such ligands include:
halogenides (e.g. chloride and fluoride),
hydrogen,
$triC_{1-12}$ hydrocarbyl-silyl or -siloxy(e.g. trimethylsilyl),
$triC_{1-6}$ hydrocarbylphosphimido (e.g. triisopropylphosphimido),
$C_{1-12}$ hydrocarbyl or hydrocarbyloxy (e.g. methyl, ethyl, phenyl, benzyl and methoxy),
$diC_{1-6}$ hydrocarbylamido (e.g. dimethylamido and diethylamido), and
5 to 7 ring membered heterocyclyl (e.g. pyrrolyl, furanyl and pyrrolidinyl).

The siloxy or germyloxy indenyl or indenyloid ligands used according to the various aspects of the invention may be prepared by any convenient means, for example by reaction of a corresponding indanone, or analogue thereof (for example a 9-fluorenone) in which a 6-membered ring fused to the 5-membered ring is directly or indirectly substituted with a hydroxyl group. Such compounds (e.g. 2-hydroxy-9-fluorenone and 4- and 5-hydroxy-indanone, which may be purchased from Aldrich) are commercially available. Alternatively, appropriate hydroxy-substituted indenes or other polycyclic structures containing the indene skeleton and with one or more appropriate hydroxyl groups, may be used as starting materials.

These starting materials may be reacted with a compound of formula $(R^1)_3QHal$ wherein $R^1$ and Q are as defined above and Hal is an appropriate halide, for example chloride, bromide or iodide (chloride being preferred) in a suitable solvent, for example N,N-dimethyl formamide (DMF) or dichloromethane.

Covalent catalysis may be used to assist in such reactions, e.g. effective quantities of triethylamine, 1,8-diazobicyclo [5,6,0]undec-7-ene (DBU) or imidazole may be employed.

Where the starting materials comprise more than one hydroxyl group such reactions permit the formation of mono- or bis-substituted siloxy or germyloxy compounds. Moreover, it is also possible to react an appropriate starting indanone, for example 4-hydroxy-indan-1-one with two equivalents of compound of formula $(R^1)_3QHal$, which may or may not be the same, to afford the corresponding bis ether of 1,4-dihydroxy-ind-1-ene through trapping of the enol tautomer.

The appropriate siloxy or germyloxy compounds may then be converted by, for example, a two-step process involving converting the indanone into a hydrazone (e.g. by reaction with tosyl hydrazine), in the presence of an effective amount of sulfuric acid in methanol; followed by reaction of the so-formed hydrazone with an appropriate base, e.g. an organolithium compound, such as methyllithium or butyllithium. The parent reaction here is commonly known as the Shapiro reaction. Particular bases of use in this regard include t-BuLi, n-BuLi, lithium diisopropylamide, t-BuOK, trialkylamines, dialkyl-magnesium, alkylmagnesium chloride, alkyl CuLi and dialkyl zinc which may be used in conjunction with a suitable solvent. If necessary, a donor such as dimethoxyethane may be added to the reaction medium containing the hydrazone prior to addition of the base.

Alternatively, the keto group in the indanone may simply be reduced under standard conditions (e.g. sodium borohydride in methanol and/or tetrahydrofuran (THF)) followed by dehydration to form the desired indene or indene skeleton-containing compound.

If the formation of a bisindenyl or bisindenyloid ligand (i.e. a "handcuff" ligand as herein before defined) is desirable, two equivalents (which may or may not be the same) of 1H- or 3H-indene etc. may be reacted with an appropriate base, e.g. an organolithium compound, such as methyllithium or butyllithium. Particular bases and solvents of use in this regard are as hereinbefore defined. If necessary, a donor such as dimethoxyethane may be added to the reaction medium containing the appropriate 1H- or 3H-indene etc. prior to addition of the base.

The anion or anions, as appropriate, may be reacted with a molecule of formula $LG_1$—L—$LG_2$ (wherein L is as hereinbefore defined and $LG_1$ and $LG_2$ represent any appropriate leaving groups which may or may not be the same, for example bromide, tosyl, chloride etc., whereby to form the desired bisindenyl ligand. Alternatively, a "handcuff" ligand may be formed by a two step process in which one equivalent of a first indenyl anion is reacted with one equivalent of $LG_1$—L—$LG_2$ and the resultant indene or equivalent molecule substituted with —L—$LG_2$ may be reacted with a second molecule anion whereby to form the desired bis indenyl/bis indenyloid ligand.

Alternatively, wherein $R^3$ is of formula —L—Z, the indenyl to indenyl bridging may be achieved using the methods disclosed in WO96/38458 (Montell).

Formation of the desired metallocene is effected by reacting the desired ligand with an appropriate quantity of base, e.g. an organolithium compound, such as methyllithium or butyllithium (i.e. where formation of a mono $\eta^5$ ligand is desired, one equivalent of base is used and where a bisindenyl ligand is being used (i.e. a bis $\eta^5$ ligand) two equivalents of base may be used. Particular bases and solvents of use in this regard are as hereinbefore defined. If necessary, a donor such as dimethoxyethane may be added to the reaction medium containing the appropriate 1H or 3H indene etc. prior to addition of the base.

The ligand can be metallated conventionally, e.g. by reaction with a halide of the metal M, preferably in an organic solvent, e.g. a hydrocarbon or a hydrocarbon/ether mixture. Bridged siloxy- or germyloxy cyclopentadienyl ligands may be constructed by reacting a siloxy- or germyloxy monocyclopentadienyl ligand with a bridging agent (e.g. $Si(CH_3)_2Cl_2$) or with a bridging agent and a further $\eta$-ligand (e.g. a different cyclopentadienyl ligand or with an indenyl, fluorenyl, etc ligand).

An alternative approach to the complexes is also envisaged where the siloxycyclopentadiene is reacted with $Zr(NMe_2)_4$ or $Zr(CH_2Ph)_4$ followed by $Me_3SiCl$ to yield the complex directly. Also, trimethylsilyl (siloxy) cyclopentadiene reacts with $ZrCl_4$ to afford the complex directly.

σ-ligands other than chlorine may be introduced by displacement of chlorine from an η-ligand metal chloride by reaction with appropriate nucleophilic reagent (e.g. methyl lithium or methylmagnesium chloride) or using, instead of a metal halide, a reagent such as tetrakisdimethylamidotitanium or metal compounds with mixed chloro and dimethylamido ligands.

Aspects of these synthetic strategies are illustrated in the following schemes which are for illustrative purposes only:

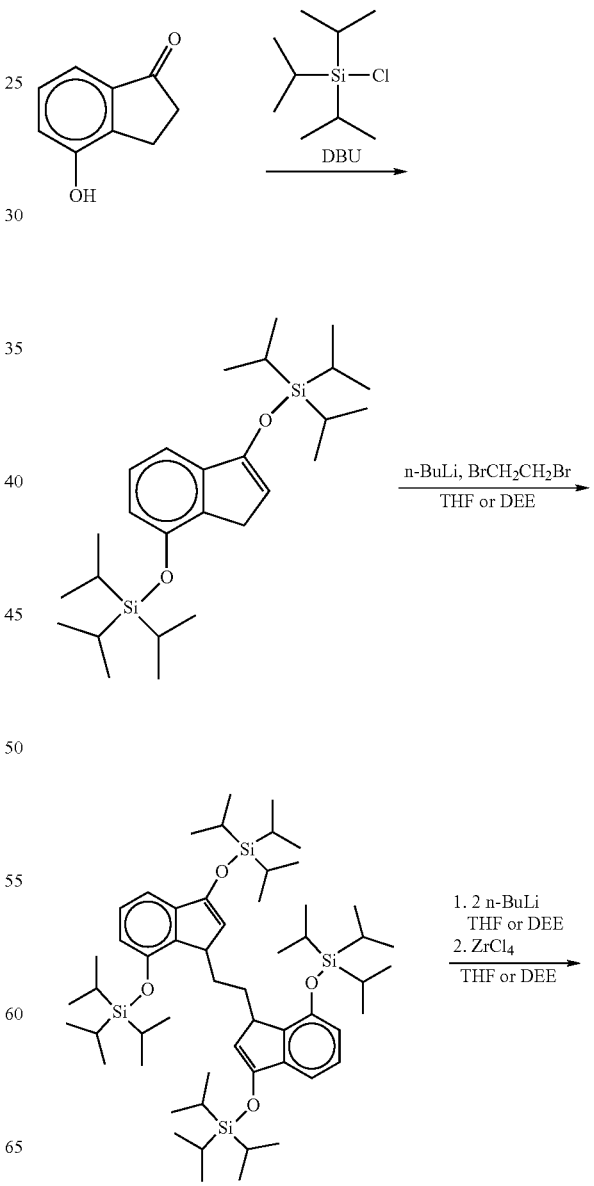

Scheme 1
Strategy for the synthesis of rac/meso-[ethylenebis(3, 7-di(tris-isopropylsiloxy)inden-1-yl)]zirconium dichloride -continued
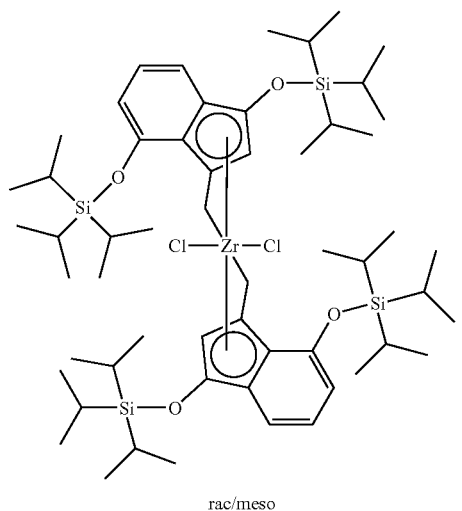
rac/meso
Scheme 2
Strategy for the synthesis of rac/meso-[ethylenebis(4,7-di(tris-isopropylsiloxy)inden-1-yl)]zirconium dichloride
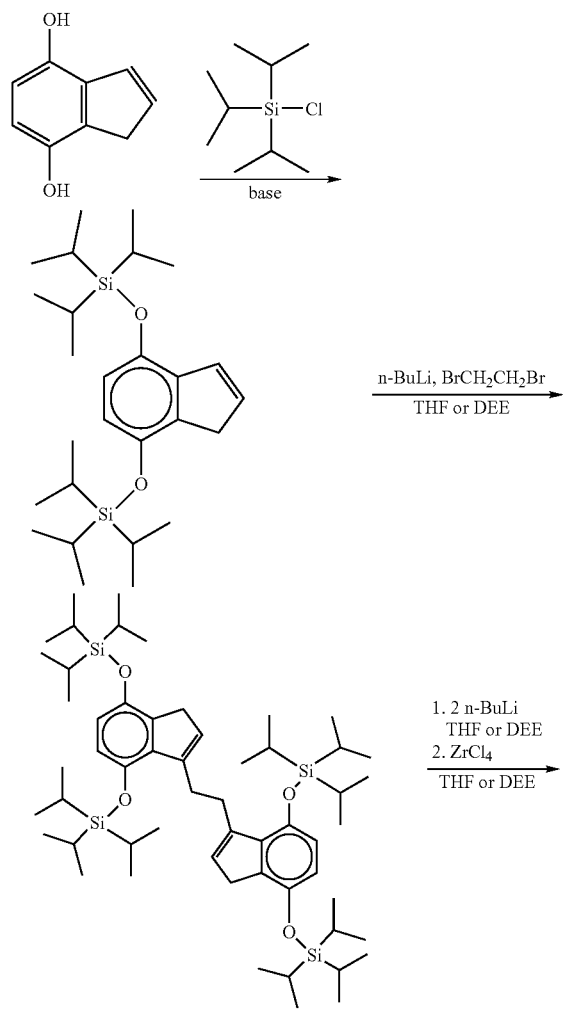
-continued
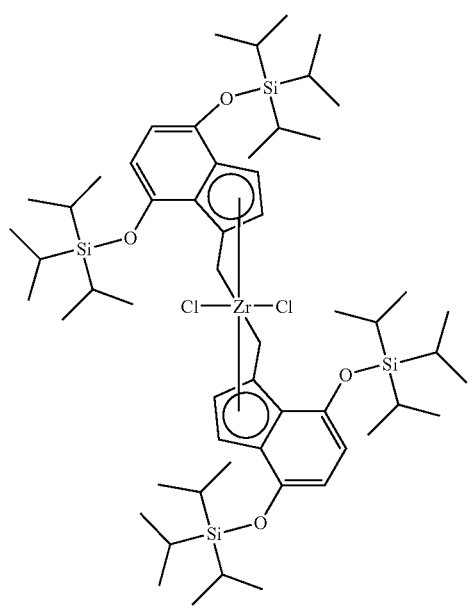
Scheme 3
Strategy for the synthesis of rac/meso-[ethylenebis(5-(tert-butyldimethylsiloxy)indenyl)]-zirconium dichloride
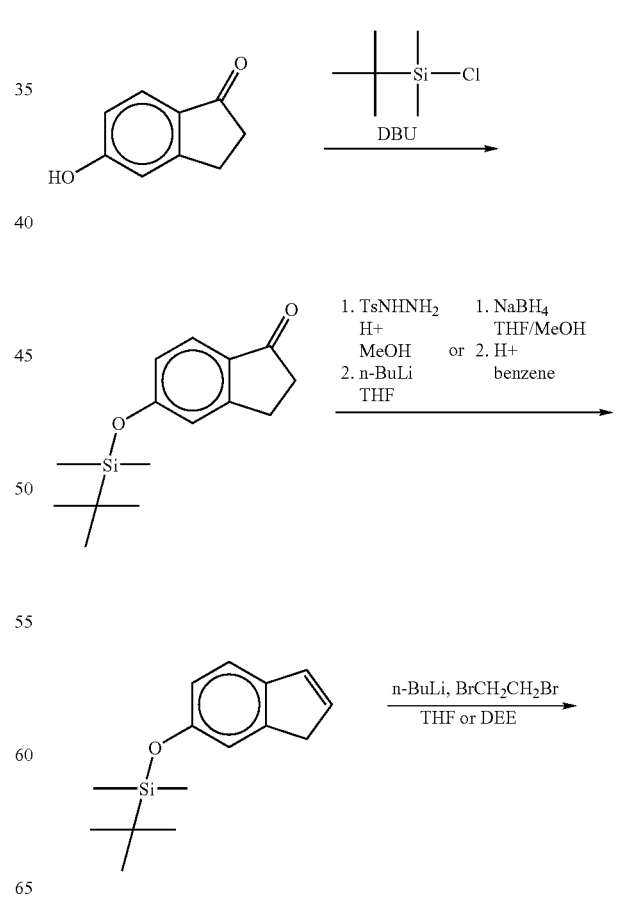

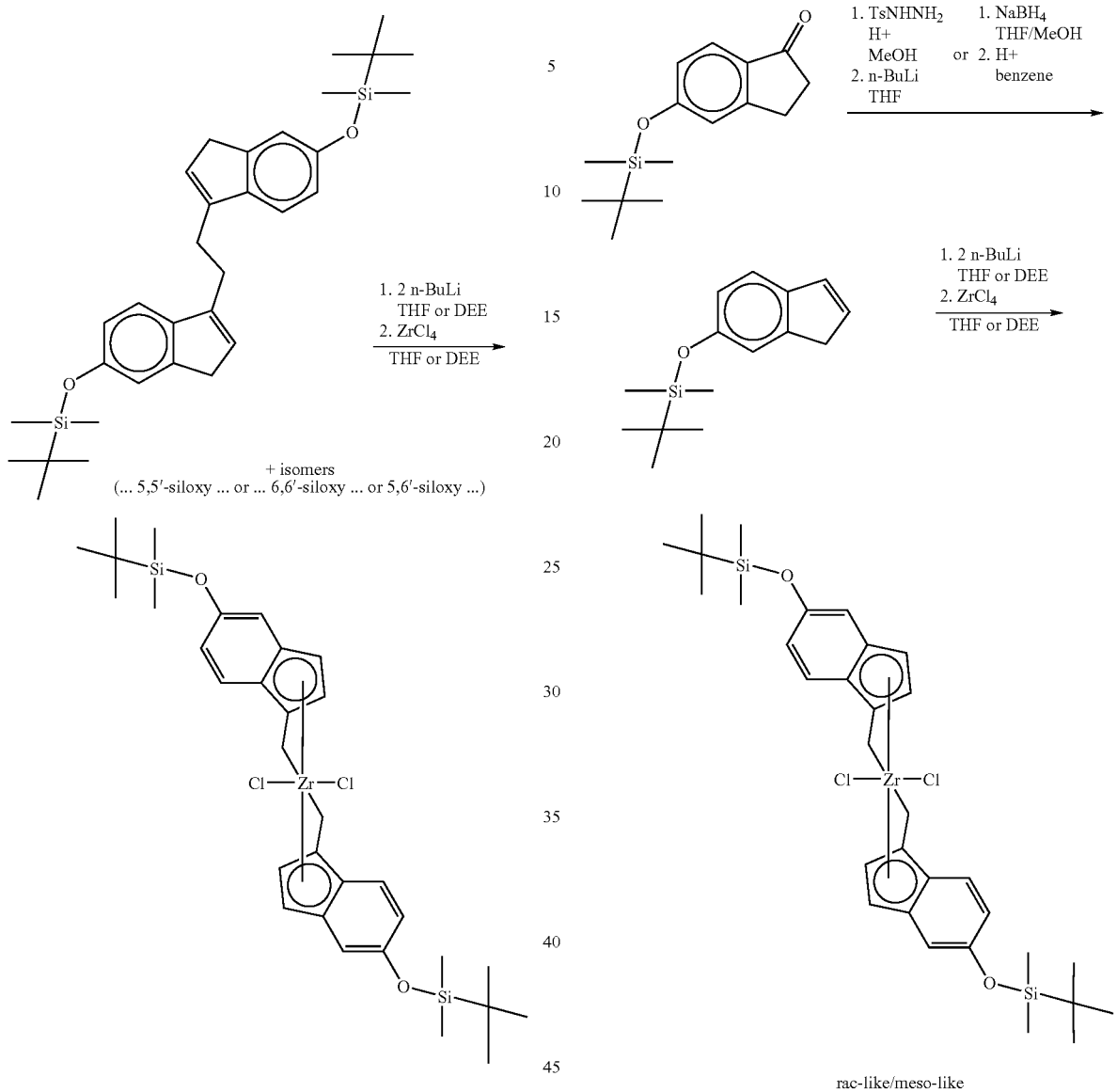
Scheme 4
Strategy for the synthesis of bis-(5-(tert-butyldimethylsiloxy)-indenyl)zirconium dichloride
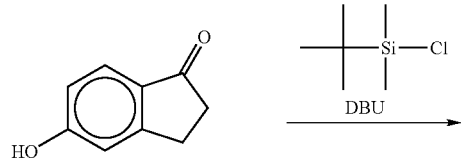
Scheme 5
Strategy for the synthesis of rac/meso-[dimethylsilylenebis(5-(tert-butyldimethylsiloxy)-indenyl)]-zirconium dichloride
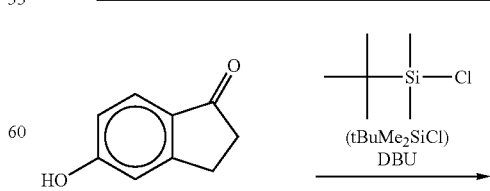

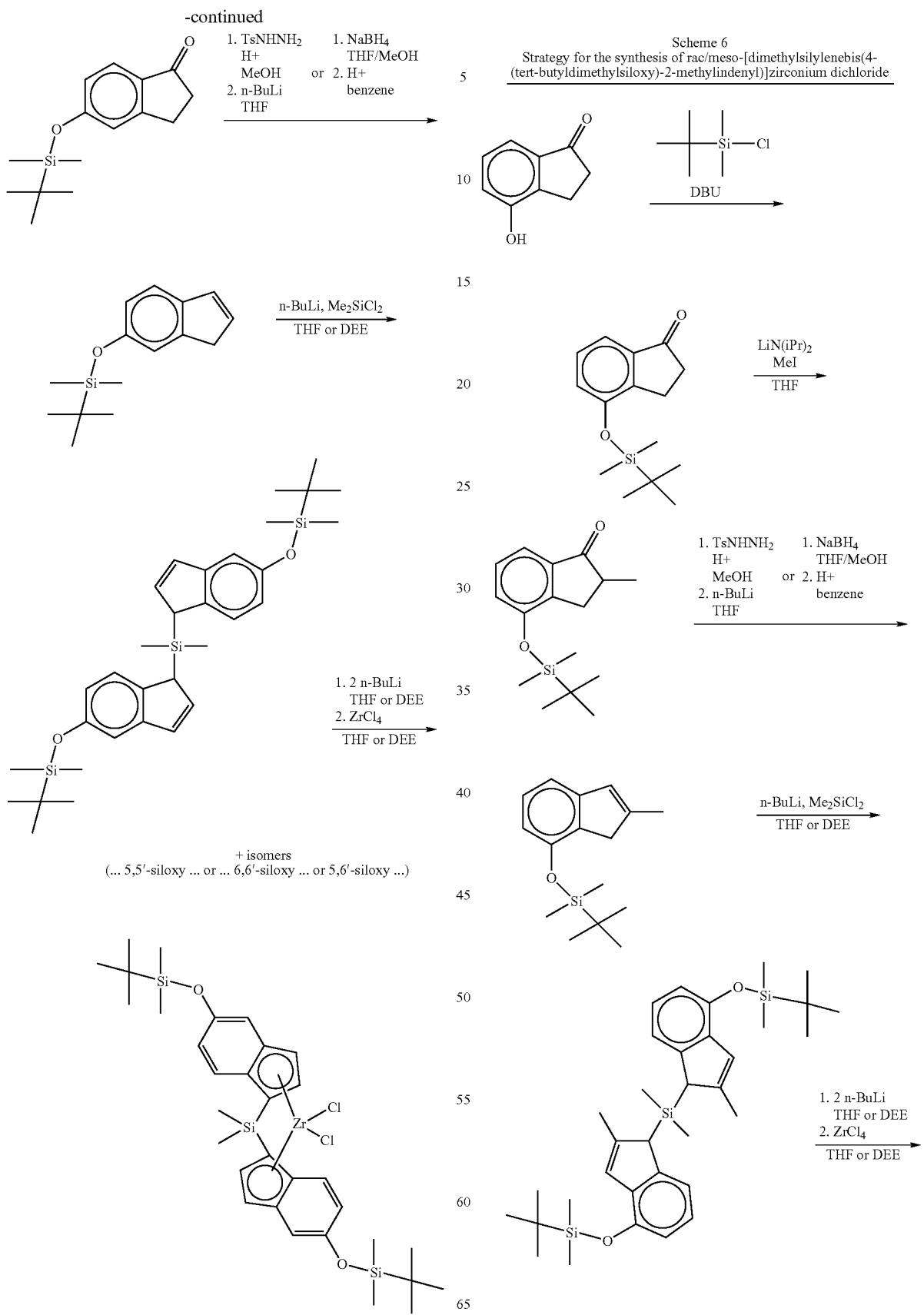

-continued
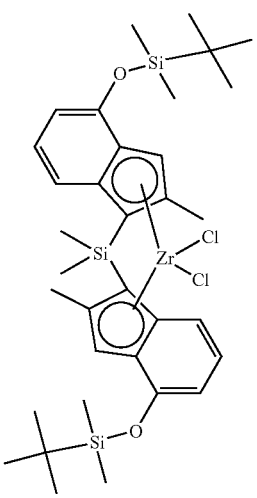
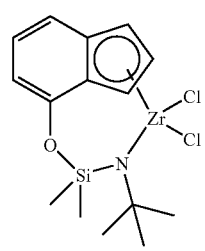
Scheme 8
Strategy for the synthesis of rac/meso-[dimethylsilylenebis(4-diisoproylhexenylsiloxy)-2-methylindenyl)]zirconium dichloride
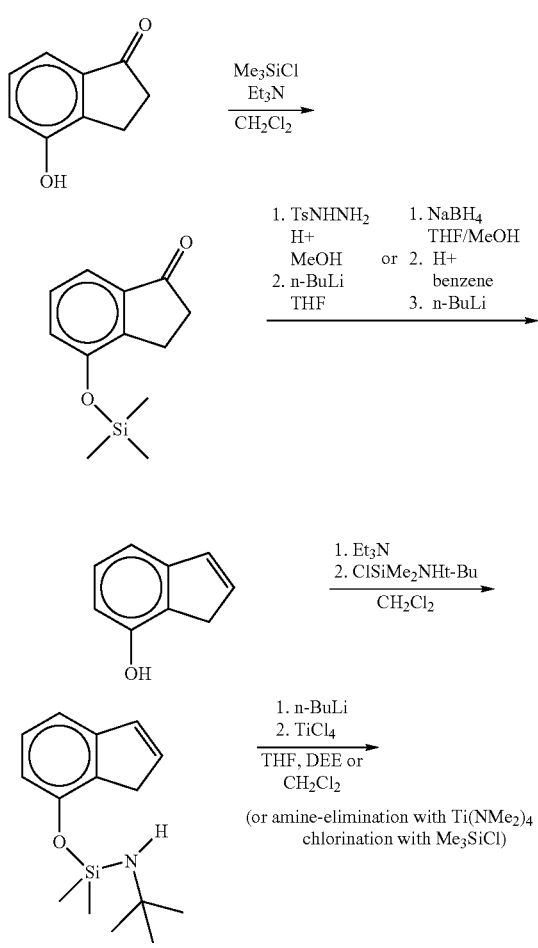
Scheme 7
Strategy for the synthesis of (N-tert-butylamido)(dimethyl)(η⁵-inden-4-yloxy)silanetitanium dichloride
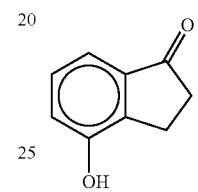
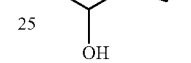
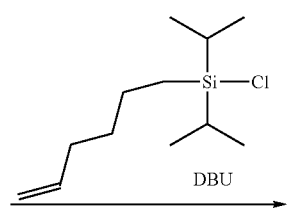

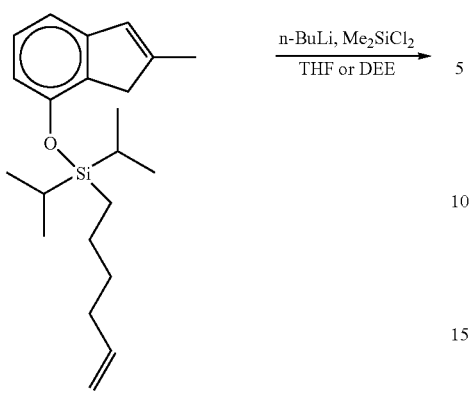
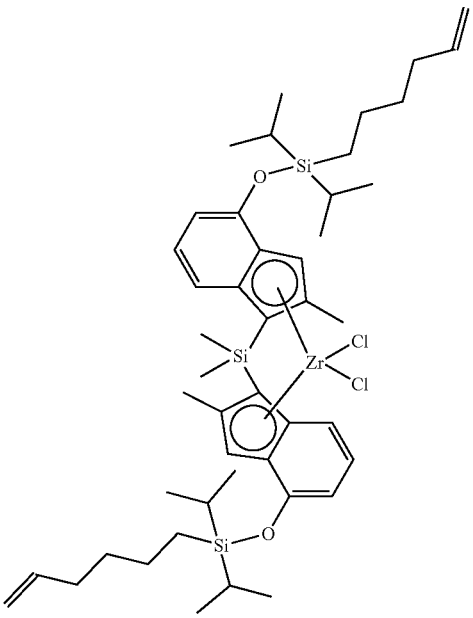
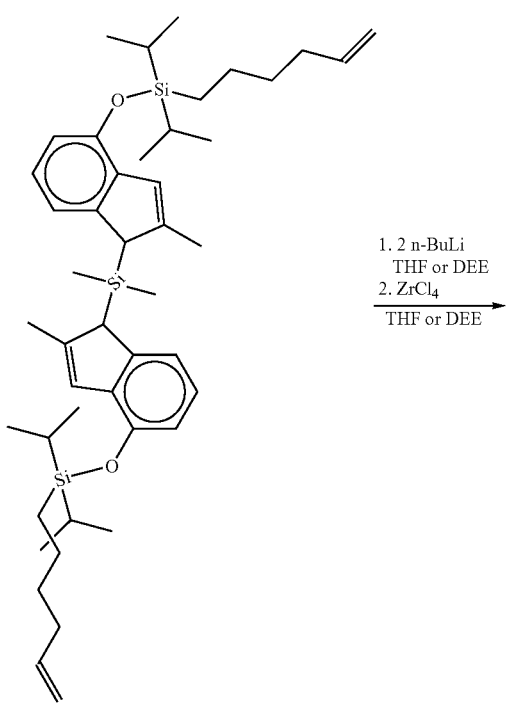
Scheme 9
Strategy for the synthesis of rac-
[dimethylsilylenebis(4-(tert-butyldimethylsiloxy)-2-methylindenyl)]zirconium dichloride
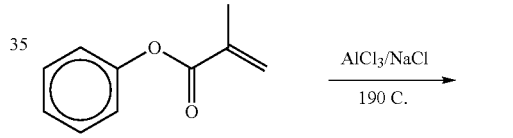
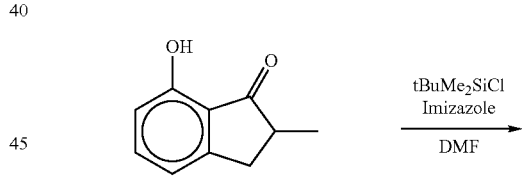
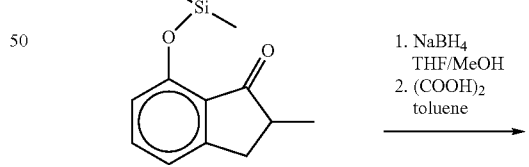
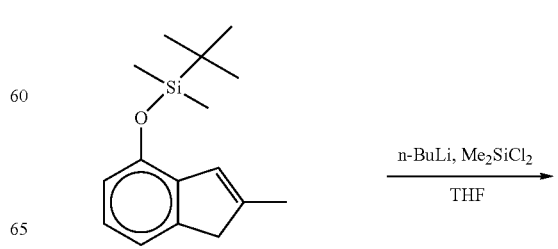

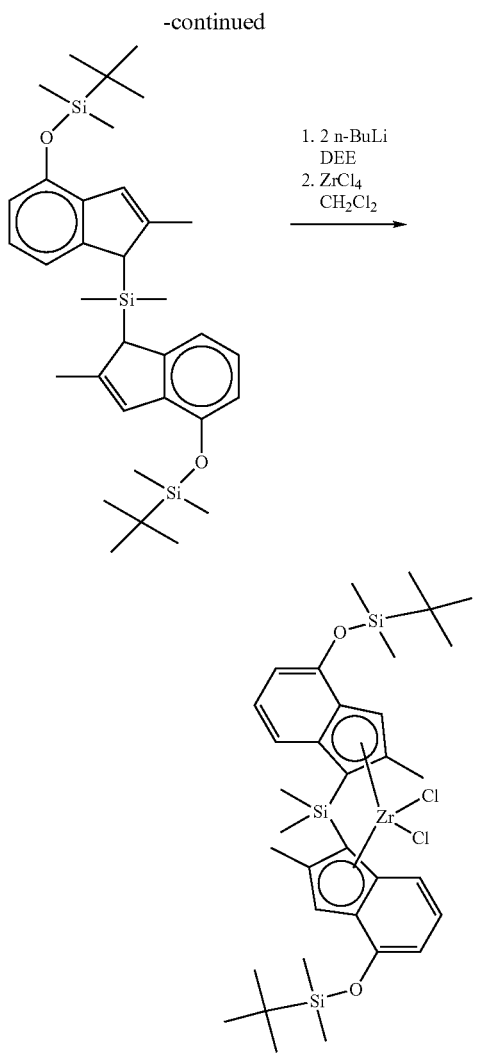

Scheme 10
Strategy for the synthesis of (N-tert-butylamido)(dimethyl)(η⁵-inden-4-yloxy)silanezirconium dichloride

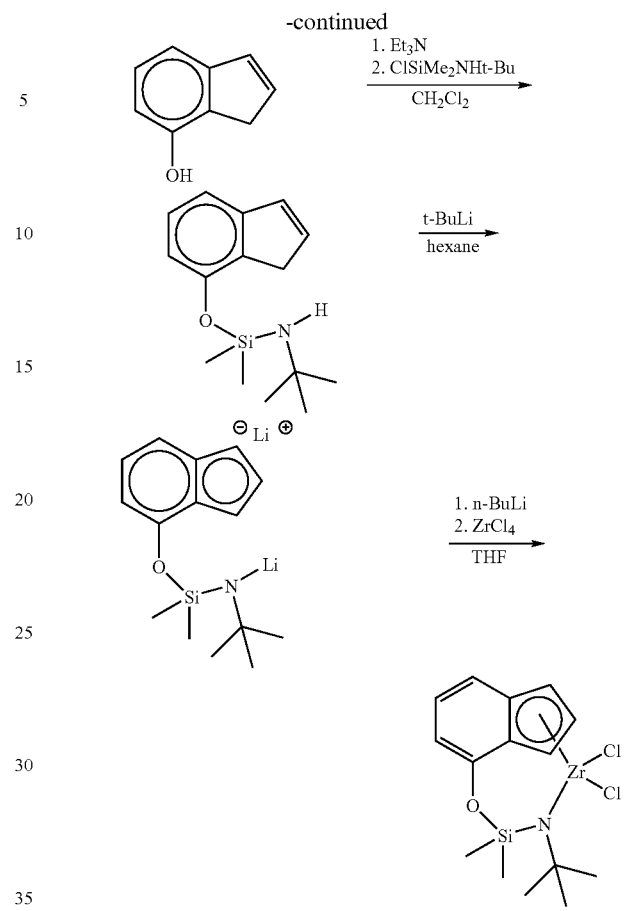

The cocatalyst of scheme 6 is particularly suitable in the preparation of isotactic polypropylene and the cocatalyst of scheme 7 is particularly suitable in high temperature production of polypropylenes.

The metallocene catalyst and cocatalyst may be introduced into the polymerization reactor separately or together or, more preferably they are pre-reacted and their reaction product is introduced into the polymerization reactor.

As mentioned above, the olefin polymerisation catalyst system of the invention comprises (i) a metallocene catalyst in which the metal is coordinated by a $\eta^5$ cyclopentadienyl ligand which forms part of an indenyl or indenyloid moiety, characterised in that said moiety is substituted in the 4- or 7-position by a pendant siloxy or germyloxy group; and normally (ii) an aluminium alkyl compound (or other appropriate cocatalyst), or the reaction product thereof.

While the aluminium alkyl compound may be an aluminium trialkyl (e.g. triethylaluminium (TEA)) or an aluminium dialkyl halide (e.g. diethyl aluminium chloride (DEAC)), it is preferably an alumoxane, either MAO or an alumoxane other than MAO, such as an isobutylalumoxane; e.g. TIBAO (tetraisobutylalumoxane) or HIBAO (hexaisobutylalumoxane). Alternatively, however, the alkylated (e.g. methylated) metallocene catalysts of the invention may be used with other cocatalysts, e.g. boron compounds such as $B(C_6F_5)_3$, $C_6H_5N(CH_3)_2H:B(C_6F_5)_4$, $(C_6H_5)_3C:B(C_6F_5)_4$ or $Ni(CN)_4 [B(C_6F_5)_3]_4^{2-}$.

However, when the metal in the catalyst is a group 3 transition metal, i.e. Sc, Y, La or Ac, no co-activator is required since such catalyst species are already in an active form, e.g. compounds of formula $In_2ScH$ wherein In is as hereinbefore defined and comprises 2 moieties of formula (IV).

The metallocene catalyst and cocatalyst may be introduced into the polymerization reactor separately or together or, more preferably they are pre-reacted and their reaction product is introduced into the polymerization reactor.

If desired the catalyst, catalyst/cocatalyst mixture or a catalyst/cocatalyst reaction product may be used in unsupported form, e.g. metallocene and MAO can be precipitated without an actual carrier material and used as such. The metallocene catalyst or its reaction product with the cocatalyst may also be introduced into the polymerization reactor in supported form, e.g. impregnated into a porous particulate support.

The particulate support material used is preferably an organic or inorganic material, e.g. a polymer (such as for example polyethylene, polypropylene, an ethylene-propylene copolymer, another polyolefin or polystyrene or a combination thereof). Such polymeric supports may be formed by precipitating a polymer or by a prepolymerization, e.g. of monomers used in the polymerization for which the catalyst is intended. However, the support is especially preferably a metal or metalloid oxide such as silica, alumina or zirconia or a mixed oxide such as silica-alumina, in particular silica, alumina or silica-alumina.

Especially preferably the support is a porous material so that the metallocene may be loaded into the pores of the support, e.g. using a process analogous to those described in WO94/14856 (Mobil), WO95/12622 (Borealis) and WO96/00243 (Exxon). The particle size is not critical but is preferably in the range 5 to 200 μm, more preferably 20 to 80 μm.

Before loading, the particulate support material is preferably calcined, i.e. heat treated, preferably under a non-reactive gas such as nitrogen. This treatment is preferably at a temperature in excess of 100° C., more preferably 200° C. or higher, e.g. 200–800° C., particularly about 300° C. The calcination treatment is preferably effected for several hours, e.g. 2 to 30 hours, more preferably about 10 hours.

The support may be treated with an alkylating agent before being loaded with the metallocene. Treatment with the alkylating agent may be effected using an alkylating agent in a gas or liquid phase, e.g. in an organic solvent for the alkylating agent. The alkylating agent may be any agent capable of introducing alkyl groups, preferably $C_{1-6}$ alkyl groups and most especially preferably methyl groups. Such agents are well known in the field of synthetic organic chemistry. Preferably the alkylating agent is an organometallic compound, especially an organoaluminium compound (such as trimethylaluminium (TMA), dimethyl aluminium chloride, triethylaluminium) or a compound such as methyl lithium, dimethyl magnesium, triethylboron, etc.

The quantity of alkylating agent used will depend upon the number of active sites on the surface of the carrier. Thus for example, for a silica support, surface hydroxyls are capable of reacting with the alkylating agent. In general, an excess of alkylating agent is preferably used with any unreacted alkylating agent subsequently being washed away.

Following treatment of the support material with the alkylating agent, the support is preferably removed from the treatment fluid and any excess treatment fluid is allowed to drain off.

The optionally alkylated support material is loaded with the catalyst. This loading may be effected by using a solution of the catalyst in an organic solvent therefor, e.g. as described in the patent publications referred to above. Preferably, the volume of catalyst solution used is from 50 to 500% of the pore volume of the carrier, more especially preferably 80 to 120%. The concentration of catalyst compound in the solution used can vary from dilute to saturated depending on the amount of metallocene active sites that it is desired be loaded into the carrier pores.

The active metal (i.e. the metal of the catalyst) is preferably loaded onto the support material at from 0.1 to 4% preferably 0.5 to 3.0%, especially 1.0 to 2.0% by weight metal relative to the dry weight of the support material.

After loading of the catalyst onto the support material, the loaded support may be recovered for use in olefin polymerization, e.g. by separation of any excess catalyst solution and if desired drying of the loaded support, optionally at elevated temperatures, e.g. 25 to 80° C.

Alternatively, a cocatalyst, e.g. an alumoxane or an ionic catalyst activator (such as a boron or aluminium compound, especially a fluoroborate) may also be mixed with or loaded onto the catalyst support material. This may be done subsequently or more preferably simultaneously to loading of the catalyst, for example by including the cocatalyst in the solution of the catalyst, by contacting the catalyst loaded support material with a solution of the cocatalyst or catalyst activator, e.g. a solution in an organic solvent, or by first impregnating the cocatalyst with a support and then contacting the cocatalyst impregnated support with a solution of the catalyst or neat catalyst (e.g. as described in WO96/32423). Alternatively however any such further material may be added to the catalyst-loaded support material in the polymerization reactor or shortly before dosing of the catalyst material into the reactor.

In this regard, as an alternative to an alumoxane it may be preferred to use a fluoroborate catalyst activator for the alkylated catalysts, especially a $B(C_6F_5)_3$ or more especially a $^{\ominus}B(C_6F_5)_4$ compound, such as $C_6H_5N(CH_3)_2H:B(C_6F_5)_4$ or $(C_6H_5)_3C:B(C_6F_5)_4$. Other borates of general formula $(cation)_a(borate)_b$ where a and b are positive numbers, may also be used.

As an alternative to the loading of the optionally alkylated support material with a solution of the procatalyst in an organic solvent, loading of the catalyst may be effected by mixing it with the optionally alkylated support material in the absence of solvents with said carrier at a temperature of at least 50° C. but less than the vaporisation temperature of the metallocene compound. The particular features of this method are disclosed in WO 96/32423 (Borealis). If use of a cocatalyst/catalyst activator in such process is desired, this may be impregnated into the optionally alkylated support material prior to loading of the catalyst.

Where such a cocatalyst or catalyst activator is used, it is preferably used in a mole ratio to the metallocene of from 0.1:1 to 10000:1, especially 1:1 to 50:1, particularly 1:2 to 30:1. More particularly, where an alumoxane cocatalyst is used, then for an unsupported catalyst the aluminium:metallocene metal (M) molar ratio is conveniently 2:1 to 10000:1, preferably 50:1 to 1000:1. Where the catalyst is supported the Al:M molar ratio is conveniently 2:1 to 10000:1 preferably 50:1 to 400:1. Where a borane cocatalyst (catalyst activator) is used, the B:M molar ratio is conveniently 2:1 to 1:2, preferably 9:10 to 10:9, especially 1:1. When a neutral triarylboron type cocatalyst is used the B:M molar ratio is typically 1:2 to 500:1, however some aluminium alkyl would normally also be used. When using ionic tetraaryl borate compounds, it is preferred to use carbonium rather than ammonium counterions or to use B:M molar ratio 1:1.

Where the further material is loaded onto the catalyst loaded support material, the support may be recovered and if desired dried before use in olefin polymerization.

The olefin polymerized in the method of the invention is preferably ethylene or an alpha-olefin or a mixture of ethylene and an α-olefin or a mixture of alpha olefins, for example $C_{2-20}$ olefins, e.g. ethylene, propene, n-but-1-ene, n-hex-1-ene, 4-methyl-pent-1-ene, n-oct-1-ene etc. The olefins polymerized in the method of the invention may include any compound which includes unsaturated polymerizable groups. Thus for example unsaturated compounds, such as $C_{6-20}$ olefins (including cyclic and polycyclic olefins (e.g. norbornene)), and polyenes, especially $C_{6-20}$ dienes, may be included in a comonomer mixture with lower olefins, e.g. $C_{2-5}$ α-olefins. Diolefins (i.e. dienes) are suitably used for introducing long chain branching into the resultant polymer. Examples of such dienes include α, ω linear dienes such as 1,5-hexadiene, 1,6-heptadiene, 1,8-nonadiene, 1,9-decadiene, etc.

In general, where the polymer being produced is a homopolymer it will preferably be polyethylene or polypropylene. Where the polymer being produced is a copolymer it will likewise preferably be an ethylene or propylene copolymer with ethylene or propylene making up the major proportion (by number and more preferably by weight) of the monomer residues. Comonomers, such as $C_{4-6}$ alkenes, will generally be incorporated to contribute to the mechanical strength of the polymer product.

Usually metallocene catalysts yield relatively narrow molecular weight distribution polymers; however, if desired, the nature of the monomer/monomer mixture and the polymerization conditions may be changed during the polymerization process so as to produce a broad bimodal or multimodal molecular weight distribution (MWD) in the final polymer product. In such a broad MWD product, the higher molecular weight component contributes to the strength of the end product while the lower molecular weight component contributes to the processability of the product, e.g. enabling the product to be used in extrusion and blow moulding processes, for example for the preparation of tubes, pipes, containers, etc.

A multimodal MWD can be produced using a catalyst material with two or more different types of active polymerization sites, e.g. with one such site provided by the metallocene on the support and further sites being provided by further catalysts, e.g. Ziegler catalysts, other metallocenes, etc. included in the catalyst material.

Polymerization in the method of the invention may be effected in one or more, e.g. 1, 2 or 3, polymerization reactors, using conventional polymerization techniques, e.g. gas phase, solution phase, slurry or bulk polymerization.

In general, a combination of slurry (or bulk) and at least one gas phase reactor is often preferred, particularly with the reactor order being slurry (or bulk) then one or more gas phase.

For slurry reactors, the reaction temperature will generally be in the range 40 to 110° C. (e.g. 85–110° C.), the reactor pressure will generally be in the range 5 to 80 bar (e.g. 50–65 bar), and the residence time will generally be in the range 0.3 to 5 hours (e.g. 0.5 to 2 hours). The diluent used will generally be an aliphatic hydrocarbon having a boiling point in the range −70 to +100° C. In such reactors, polymerization may if desired be effected under supercritical conditions.

For gas phase reactors, the reaction temperature used will generally be in the range 60 to 115° C. (e.g. 70 to 110° C.), the reactor pressure will generally be in the range 10 to 25 bar, and the residence time will generally be 1 to 8 hours. The gas used will commonly be a non-reactive gas such as nitrogen together with monomer (e.g. ethylene).

For solution phase reactors, the reaction temperature used will generally be in the range 130 to 270° C., the reactor pressure will generally be in the range 20 to 400 bar and the residence time will generally be in the range 0.005 to 1 hour. The solvent used will commonly be a hydrocarbon with a boiling point in the range 80–200° C.

Generally the quantity of catalyst used will depend upon the nature of the catalyst, the reactor types and conditions and the properties desired for the polymer product. Conventional catalyst quantities, such as described in the publications referred to herein, may be used.

The invention will now be illustrated by reference to the following non-limiting Examples:

Ligand and Complex Synthesis

All operations are carried out under an argon or nitrogen atmosphere using standard Schlenk, vacuum and drybox techniques. Ether, tetrahydrofuran (THF) and toluene solvents were dried with potassium benzophenone ketyl and distilled under argon prior to use. Other solvents were dried using 13X+13 Å molecular sieves. All other chemicals were used as commercially available.

NMR spectra were recorded using a JEOL JNM-EX270 MHz FT-NMR spectrometer with tetramethylsilane (TMS) as an internal reference.

Direct inlet mass spectra were recorded using a VG TRIO 2 quadruple mass spectrometer in electron impact ionization mode (70eV).

GC-MS analysis was performed using a Hewlett Packard 6890/5973 Mass Selective Detector in electron impact ionization mode (70eV), equipped with a silica capillary column (30 m×0.25 mm i.d).

EXPERIMENTAL; Complex Synthesis

General Considerations. All reactions with organometallic reagents were carried out in an argon atmosphere using standard Schlenk techniques. Solvents were dried and distilled under argon prior to use. Merck Silica 60 (0.1% Ca) was employed in chromatographic purifications.

Preparation of rac-[ethylenebis(4-(tert-butyldimethylsiloxy)-indenyl]-zirconium dichloride (5)

4-(tert-Butyldimethylsiloxy)-1-indanone (1). To a solution of 4-hydroxy-1-indanone (25.0 g, 169 mmol) and imidazole (28.7 g, 422 mmol) in DMF (500 ml) was added tert-butyldimethylchiorosilane. The reaction mixture was stirred overnight at room temperature and treated with water (500 ml) and extracted with diethyl ether (500 ml). The organic phase was collected and dried over sodium sulfate. Evaporation gave a yellow oil which was distilled under reduced pressure to give indanone (1) (35.44 g, 135 mmol, 79.9%) as a colourless oil (120–121° C./0.1 mbar).

4-(tert-Butyldimethylsiloxy-1-indanone tosylhydrozone (2). To a solution of indanone (1) (30.0 g, 114 mmol) in methanol (1000 ml) was added p-toluenesulfonyl-hydrazide (21.29 g, (114 mmol) and 10 drops of concentrated sulfuric acid. The reaction mixture was then heated under reflux for 3 hours, whereafter the solution was concentrated and a crystallization followed overnight at room temperature. The crystalline tosylhydrozone (2) (40.38 g, 93.8 mmol, 82.2%) was isolated by filtration.

4-(tert-Butyldimethylsiloxy)-indene (3). To a solution of tosylhydrozone (2) (34.87 g, 81 mmol) in THF (350 ml) at 0° C. was added dropwise n-butyllithium (99 ml, 247 mmol, 2.5 M solution in hexane). After the addition was complete the solution was stirred at room temperature overnight. The reaction solution was then treated with ice water (400 ml) and acidified with hydrochloric acid (5% solution). The acidic solution was extracted with diethyl ether (3×250 ml), the organic fractions were combined and washed successively with aqueous sodium bicarbonate solution and brine, and dried over sodium sulfate. The solvents were removed by evaporation and the remaining yellow oil was distilled under reduced pressure to give indene (3) (6.94 g, 28.2 mmol, 34.8%) as a pale yellow oil (82–83° C./0.2 mbar) as a mixture of two doublebond (1 H and 3 H) isomers.

Bis(4-(tert-butyldimethylsiloxy)-1-indenyl) ethane (4). To an ice cooled solution of indene (3) (8.5 g, 34.5 mmol) in THF (50 mL) was added n-BuLi (15.2 ml, 37.9 mmol, 2.5 M solution in hexane) and the reaction mixture stirred for two hours at room temperature. The solution was then cooled to −80° C. and a solution of dibromoethane (3.24 g. 17.3 mmol) in THF. (15 ml) was added dropwise. After addition was complete, the temperature of the reaction solution was slowly allowed to rise to room temperature and stirred overnight. The resulting solution was washed with saturated ammonium chloride solution (100 ml) and extracted with diethyl ether (2×100 ml). The organic fractions were combined and dried over sodium sulfate. Solvents were evaporated and the remaining oil was dissolved in a methanol/acetone mixture (3:1), cooling to −30° C. gave (4) (0.68 g, 7.6%) as a yellowish crystalline solid.

Rac-[ethylenebis (4-(tert-butyldimethylsiloxy)-indenyl]-zirconium dichloride (5). To a solution of (4) (0.68 g, 1.3 mmol) in THF (25 mL) at 0° C. was added dropwise n-BuLi (1.05 ml, 2.63 mmol, 2.5 M solution in hexane), and the reaction mixture was stirred for three hours at room temperature. The resulting solution was added dropwise to a suspension of $ZrCl_4$ (0.39 g, 1.7 mmol) in THF (25 mL) at −80° C. The reaction mixture was gradually warmed to room temperature and stirred overnight. The solvents were evaporated, the remaining solid was extracted with $CH_2Cl_2$ (100 ml) and filtrated through Celite to remove lithium chloride. The solvent was evaporated and the crude product was extracted with diethyl ether (200 ml) and filtrated through Celite. Concentration and cooling to −30° C. gave (5) (50 mg, 5.6%) as yellow microcrystals.

This reaction sequence is depicted in Diagram 1 below.

Diagram 1.
Synthesis of rac-[ethylenebis(4-(tert-butyldimethylsiloxy)-indenyl)]-zirconium dichloride.

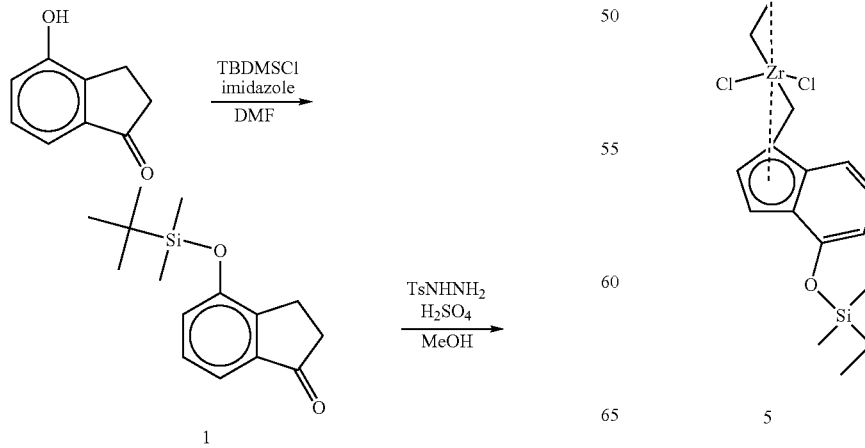

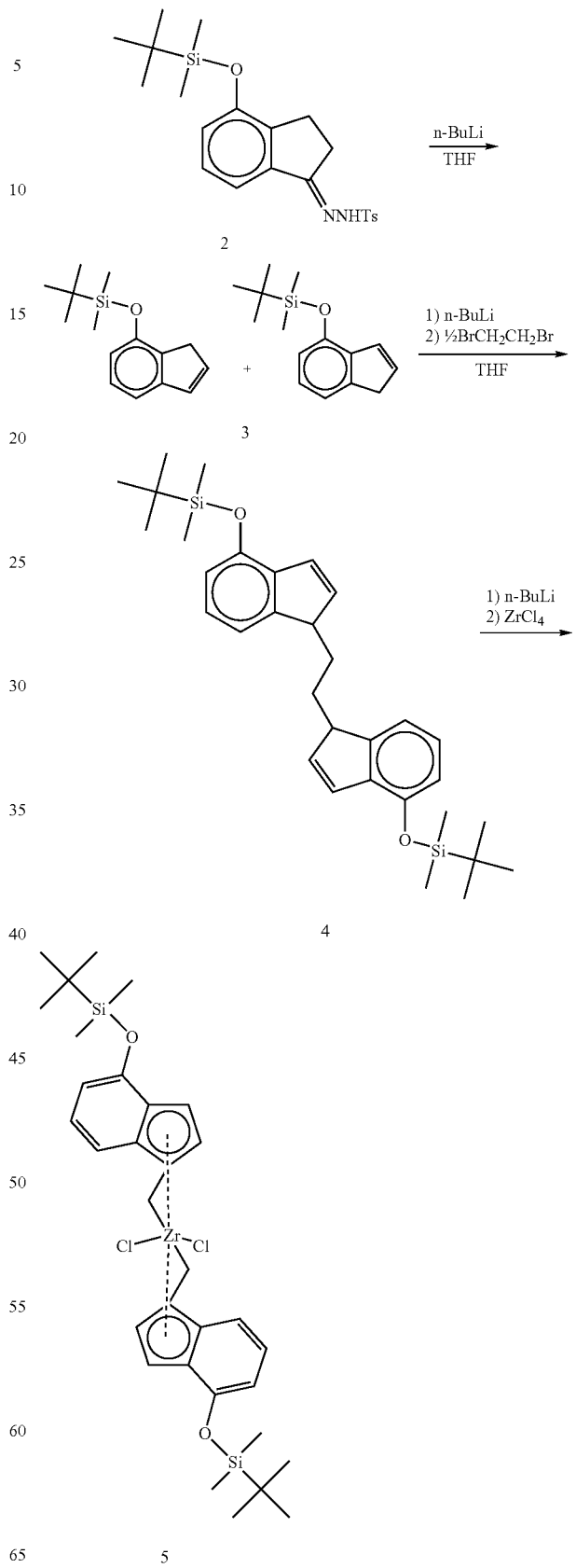

Preparation of rac-[dimethylsilylenebis(4-(tert-butyldimethylsiloxy)-2-methyl-indenyl)]-zirconium dichloride (10)

7-hydroxy-2-methyl-1-indanone (6) was prepared according to the procedure described by Bringmann and Jansen (Liebigs Ann. Chem. 1985, 2116–2125).

7-(tert-butyldimethylsiloxy)-2-methyl-1-indanone (7). To a solution of 7-hydroxy-2-methyl-1-indanone (6) (10.2 g, 37 mmol) and imidazole (3.02 g, 44 mmol) dissolved in DMF (200 ml) was added tert-butyldimethylchlorosilane (6.11 g, 41 mmol) in DMF (50 ml). The reaction mixture was stirred overnight at room temperature and treated with water (200 ml) and extracted with diethylether (2×200 ml). The combined organic phases were washed with aqueos NH$_4$Cl (300 ml), brine (100 ml) and dried over sodium sulfate. Evaporation gave (7) as a yellow oil which was used without further purification.

7-(tert-butyldimethylsiloxy)-2-methyl-1-indene (8). To a solution of 7 (13.0 g, 47.1 mmol) in THF/methanol (2:1, 500 ml) was added sodium borohydride (3.67 g, 94 mmol) in several portions. The reaction mixture was stirred at room temperature overnight. The clear colorless solution was diluted with diethylether (300 ml), washed with 5% HCl (2×300 ml), saturated aqueous NaHCO$_3$ (300 ml), brine (200 ml) and dried over anhydrous Na$_2$SO$_4$. Evaporation of volatiles gave brownish oil which was used without further purification.

The oil (11.2 g) was dissolved in toluene (300 ml) and anhydrous oxalic acid (10.8 g, 120 mmol) was added. The mixture was heated at 100° C. for 1 hour and allowed to cool to room temperature. After decanting the solution on water it was diluted with diethyl ether (400 ml). The organic phase was washed with water (300 ml), 5% HCl (2×300 ml), saturated aqueous NaHCO$_3$ (300 ml), brine (200 ml) and dried over anhydrous Na$_2$SO$_4$. The solvents were removed under reduced pressure to give brown oil. The crude product was purified by flash chromatography (99% hexane/1% ethyl acetate) to yield 8 (3.1 g) as a colorless oil.

Bis(4-(tert-butyldimethylsiloxy)-2-methyl-1-indenyl) dimethylsilane (9). To an ice cooled solution of 8 (2.70 g, 10.4 mmol) in THF (50 mL) was added n-BuLi (4.2 ml, 10.5 mmol, 2.5 M solution in hexane) dropwise. The ice bath was removed 5 minutes after completion of the addition of n-BuLi and the reaction mixture was stirred for 40 minutes at room temperature. The orange solution was then cooled to 0° C. and a solution of dichlorodimethylsilane (0.67 g, 5.2 mmol) in THF (5 ml) was dropwise added. The reaction mixture was slowly allowed to attain room temperature and stirred overnight. The resulting solution was washed with saturated ammonium chloride solution (100 ml) and extracted with diethyl ether (2×100 ml). The organic fractions were combined and dried over sodium sulfate. The solvents were evaporated and the remaining oil was purified by flash chromatography (99% pentane/1% diethyl ether) to yield a mixture of rac- and meso-9 (1.91 g, 64%) as a yellow oil.

Rac-[dimethylsilylenebis(4-(tert-butyldimethylsiloxy)-2-methyl-indenyl)]-zirconium dichloride (10). To a pale yellow solution of 9 (0.42 g, 0.73 mmol) in Et$_2$O (15 mL) at −40° C. was added dropwise n-BuLi (0.60 ml, 1.50 mmol, 2.5 M solution in hexane) and the reaction mixture was stirred for 15 minutes at −40° C. and then at room temperature for 1.5 hours. The solvent was removed in vacuo and the resulting yellowish powder was mixed with ZrCl$_4$ (0.17 g, 0.73 mmol). Precooled CH$_2$Cl$_2$ (−80° C., 50 ml) was added at −80° C. The resulting red suspension was gradually warmed to room temperature and stirred overnight. The resulting red solution was filtered through Celite to remove lithium chloride and the solvent was evaporated. The crude product was extracted with Et$_2$O, concentrated and cooled to −30° C. to give 10 as an orange powder.

This reaction sequence is depicted in Diagram 2 below.

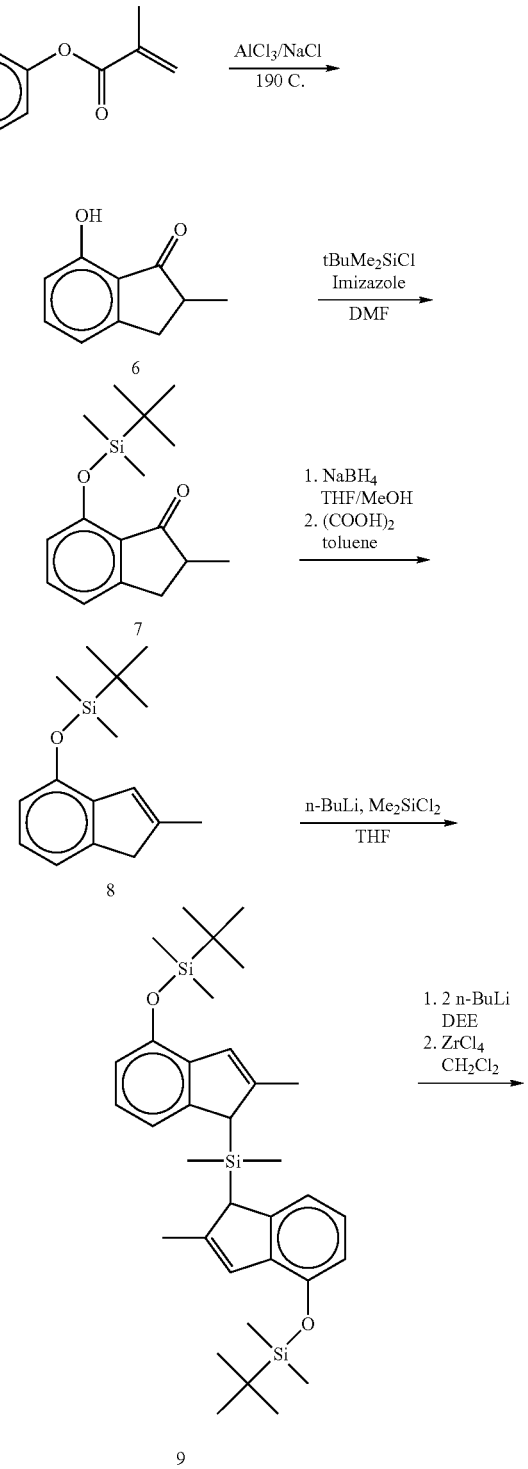

Diagram 2.
Synthesis of rac-[dimethylsilylenebis(4-tert-buyldimethylsiloxy)-2-methyl-indenyl)]-zirconium dichloride.

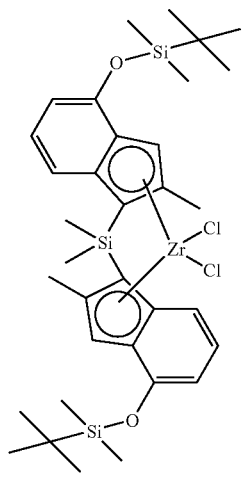

10

Preparation of [(N-tert-butyl-amido)-dimethyl-($\eta^5$-inden-4-yloxy)-silane)]-titanium dichloride (15)

4-(tert-Butyldimethylsiloxy)-1-indanone (1). To a solution of 4-hydroxy-1-indanone (25.0 g, 169 mmol) in DMF (500 ml) was triethylamine (22.2 g, 220 mmol) added, to the resulting solution was tert-butyldimethylchlorosilane (28.0 g, 186 mmol) added. The reaction mixture was stirred overnight at room temperature and treated with water (500 ml) and extracted with diethyl ether (500 ml). The organic phase was collected and dried over sodium sulfate. Evaporation gave a yellow oil which was distilled under reduced pressure to give the indanone (36.68 g, 140 mmol, 82.7%) as a colourless oil (120–121° C./0.1 mbar).

4-Hydroxyindene (11). To a solution of 4-(tert-butyldimethylsiloxy)-1-indanone (35.0 g, 133 mmol) in methanol/THF (100 ml:200 ml) was NaBH$_4$ (7.57 g, 200 mmol) added in portions at 0° C. The reaction mixture is stirred overnight. The resulting solution is poured on ice, acidified with concentrated hydrochloric acid to pH=1 and extracted with diethyl eter (2×200 ml). The organic fractions were combined and washed with brine, water and dried over sodiumsulfate. The solvents were evaporated and the remaining oil (siloxyindanol) was dissolved in toluene (300 ml). To this solution was oxalic acid (24.0 g, 267 mmol) added. The mixture was heated under reflux for 3 hours, whereafter the reaction mixture was washed with a 10% aqueous solution of NaHCO$_3$ and dried over sodiumsulfate. The solvent was removed by evaporation. The remaining yellow oil was dissolved in THF (300 ml) and treated with tetra-n-butylammonium fluoride (69.6 g, 266 mmol) at 0° C. and stirred for 30 min at room temperature. The reaction solution was treated with a saturated NH$_4$Cl solution (200 ml) and extracted with diethyl ether (2×200 ml) The organic phase was collected, evaporation of solvent left a solid which was recrystallized from methanol to give a pale yellow solid (11.45 g, 86.6 mmol, 65.10%).

N-(tert-Butyl)-N-(1-(1H-4-indenyloxy)-1,1-dimethylsilyl)amine (12). 4-Hydroxyindene (9.25 g, 70 mmol) was dissolved in methylenechloride (200 ml) and the solution was cooled to 0° C. To this solution was triethylamine (10.7 g, 105 mmol) added. The reaction mixture was stirred for 1 h and then N-(tert-butyl)-N-(1-chloro-1,1-dimethylsilyl)amine (13.95 g, 84 mmol) added. The mixture was stirred for 2 h at 0° C. and then the flask was warmed to room temperature and stirred overnight. The solvent was then removed by evaporation and the residue was extracted with hexane (2×40 ml) and filtered. Solvent was removed under reduced pressure leaving 14.6 g (56 mmol, 79.8%) of the silylamine as a yellow liquid.

N-(tert-Butyl)-N-(1-(1H-4-indenyloxy)-1,1-dimethylsilyl)amine dilithium salt (13). To a solution of N-(tert-Butyl)-N-(1-(1H-4-indenyloxy)-1,1-dimethylsilyl)amine (13.6 g, 52 mmol) in hexane (200 ml) at 0° C. was added dropwise t-butyllithium (86 ml, 129 mmol, 1.5 M solution in pentane). The reaction mixture was stirred overnight at room temperature. The resulting off-white precipitate was collected via filtration, washed with hexane (100 ml) and dried under reduced pressure to give 9.8 g (36 mmol, 69.2%) of the dilithium salt as an off-white solid.

[(N-tert-butylamido)-dimethyl-($\eta^5$-inden-4-yloxy)-silane]-titanium dichloride (14). TiCl$_3$(THF)$_3$ (7.1 g, 19.1 mmol) was suspended in THF (50 ml). To this solution was a solution of N-(tert-butyl)-N-(1-(1H-4-indenyloxy)-1,1-dimethylsilyl)amine dilithium salt (5.2 g, 19.1 mmol) in THF (200 ml) added. The reaction solution was stirred for 1 h. To the resulting solution was PbCl$_2$ (3.45 g, 12.4 mmol) added and the solution was stirred for 1 h. The solvent was removed under reduced pressure. The residue was then extracted with toluene (50 ml), the solution was filtered, and the toluene was removed under reduced pressure. The residue was then titrated with hexane (50 ml) and the precipitate was collected via filtration, washed with hexane and dried under vacuum to give the titanium dichloride (3.72 g, 9.9 mmol, 51.6%) as an orange solid.

This reaction sequence is depicted in Diagram 3 below.

Diagram 3.
Synethesis of [(N-tert-butylamido)-dimethyl-($\eta^5$-inden-4-yloxy)-silane -titanium dichloride.

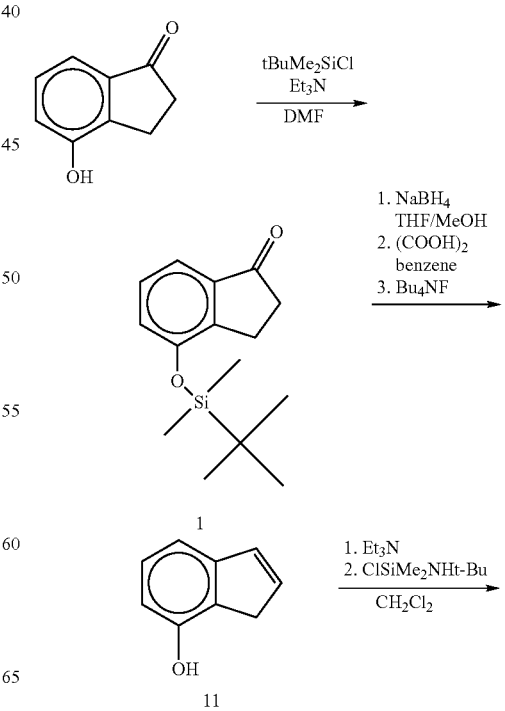

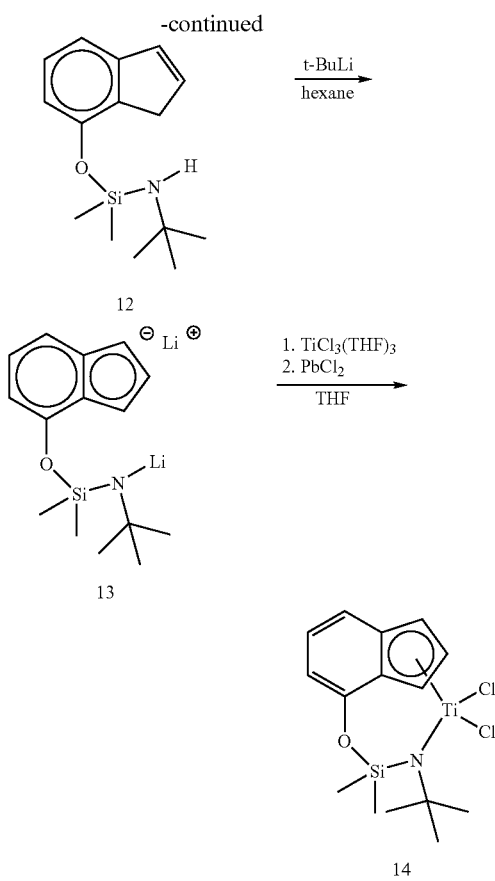

Polymerization Reactions

Ethylene (>99.95%), nitrogen (>99.999%) and n-pentane (>97%) were used. 1-Hexene was purified by refluxing over sodium and distillation under an atmosphere of nitrogen.

Catalysts were prepared by mixing the co-catalyst (30 wt % MAO in toluene or 70 wt % HIBAO in toluene, both from Albemarle) in toluene to reach the desired Aluminium: M (Metal) molar ratio.

A feeding vessel in a glove box was charged with an appropriate amount of catalyst and transferred to a stirred (400 min$^{-1}$) Büchi 2.0/3.0 L stirred autoclave reactor. The reactor was purged with nitrogen and charged with n-pentane at ambient temperature. The reactor temperature was adjusted to +80° C. and the feed of ethylene into the reactor begun. The partial pressure of ethylene ($10^6$ Pa (10.0 bar)) and total pressure ($1.3 \times 10^6$ Pa (13 bar)) were held constant by continuously feeding in monomer. After 30 minutes the reactor was vented and the polymer isolated.

When 1-hexene was used as comonomer its addition to the reactor was simultaneous with ethylene.

Table 1 below provides details of the polymerisations conducted. The catalysts used were either compound (5) (infra) or rac-[ethylenebis(2-(tertbutyldimethylsiloxy)-indenyl)]zirconium dichloride which is disclosed in WO97/28170 (infra).

TABLE 1

| Polymer type | HDPE | HDPE | LLDPE | LLDPE | HDPE | HDPE |
|---|---|---|---|---|---|---|
| Complex | Comparative example | Compound (5) of example | Comparative example | Compound (5) of example | Comparative example | Compound (5) of example |
| Catalyst amount | 0.25 μmol | 0.52 μmol | 0.27 μmol | 0.5 μmol | 0.25 μmol | 1.27 μmol |
| Polymer amount (g) | 108 | 130 | 165 | 225 | 52 | 47 |
| Polymerisation time (Min) | 30 | 60 | 30 | 30 | 30 | 60 |
| Cocatalyst | MAO | MAO | MAO | MAO | HIBAO | HIBAO |
| Aluminium/Metal ratio | 1000 | 900 | 900 | 900 | 1000 | 916 |
| Activity of metal (KgPol/g met h) | 9472 | 2766 | 13399 | 9855 | 4560 | 433 |
| Comonomer | — | — | 1-hexene | 1-hexene | — | — |
| Comonomer amount (ml) | — | — | 50.0 | 30.0 | — | — |
| Comonomer amount (w-%) | — | — | 2.4 | 3.3 | — | — |
| Medium | PENTANE | ISOBUTANE | PENTANE | ISOBUTANE | PENTANE | ISOBUTANE |
| Medium amount (ml) | 1200 | 1800 | 1200 | 1800 | 1200 | 1800 |
| Monomer | ETHENE | ETHENE | ETHENE | ETHENE | ETHENE | ETHENE |
| Pressure tot (bar) | 14 | 23 | 13 | 23 | 14 | 23 |
| Temperature (° C.) | 80 | 80 | 80 | 95 | 80 | 80 |
| CRYSTALLINITY (%) | 67 | 64 | 53 | 43 | 71 | — |
| MELTING TEMP (° C.) | 135 | 134 | 122 | 116 | 133 | — |
| MFR$_2$ (g/10 min) | n.a. | <0.1 | 1.4 | n.a. | 132 | — |
| MFR$_{21}$ (g/10 min) | 7.5 | 120 | 46.20 | 0.10 | 47.50 | — |
| BD (kg/m3) | 70.00 | — | 178 | — | 190 | — |
| T-VINYLENE (C = C/1000C) | 0.01 | 0.04 | 0.00 | 0.04 | 0.01 | — |

TABLE 1-continued

| | | | | | | |
|---|---|---|---|---|---|---|
| VINYL (C = C/1000C) | 0.50 | 0.34 | 0.53 | 0.17 | 0.62 | — |
| VINYLIDENE (C = C/1000C) | 0.02 | 0.04 | 0.03 | 0.06 | 0.01 | — |
| $M_n$ | 44300 | 63600 | 35200 | 143000 | 35700 | — |
| $M_w$ | 145000 | 270000 | 86600 | 477000 | 88700 | — |
| MWD | 3.3 | 4.2 | 2.5 | 3.3 | 2.5 | — |

The invention claimed is:

1. A metallocene catalyst of formula (III)

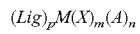

in which:

M is a transition metal ion or a lanthanide metal ion;

p is 1 or 2;

m is greater than or equal to 0;

n is greater than or equal to 0;

n+m is equal to the valency of the metal not satisfied by ligand or ligands Lig;

X is a ligand which co-ordinates to M selected from a $\eta^5$ hydrocarbyl, $\eta^1$ hydrocarbyl, halo, hydrocarbyl amino or hydrocarbyl amido ligand;

A is a σ-ligand; and each Lig is independently a negatively charged indenyl or indenyloid moiety of the following formula (IV):

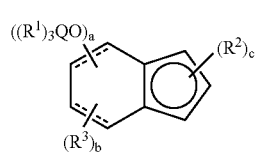

wherein one or more of the ring carbon atoms may be replaced by a ring heteroatom;

each Q is either a silicon or a germanium atom;

either or both of the bonds shown as ----- may be present or absent;

each $R^1$ which may be the same or different is a $C_{1-20}$ hydrocarbyl or a $C_{1-8}$ alkylamino at least one group $(R^1)_3QO$—being present on the 4,5,6 or 7 position;

each $R^2$ is a hydrogen or a group bonded to the 5-membered ring through a carbon, oxygen, silicon, phosphorus, germanium, nitrogen or sulfur atom;

each $R^3$ is a hydrogen or a group bonded to the 6-membered ring through a carbon, oxygen, silicon, germanium, nitrogen, phosphorus or sulfur atom; or two or more $R^2$ and/or two or more $R^3$ groups attached to adjacent ring atoms on the same ring together form a 5- to 8-membered fused ring; and optionally one $R^2$ or $R^3$ is —L—Z wherein L is a 1 to 4 atom chain and Z is a second moiety of formula (IV), a is an integer between 1 and 3, b is an integer between 1 and 3, the sum of a and b being no more than 4, c is an integer between 1 and 3, with the proviso that no more than one —L—Z group is present in each ligand.

2. The catalyst as claimed in claim 1 wherein M is a group 4 to 6 transition metal.

3. The catalyst as claimed in claim 2 wherein said metal is Cr, Ti, Zr or Hf.

4. The catalyst as claimed in claim 1 wherein p is 2 and m is zero.

5. The catalyst as claimed in claim 1 wherein each A is a halo, amido or $C_{1-12}$-hydrocarbyl ligand.

6. The catalyst as claimed in claim 5 wherein each A is a chloro ligand.

7. The catalyst as claimed in claim 1 wherein all the ring atoms are carbon atoms.

8. The catalyst as claimed in claim 1 wherein both ---- bonds are present.

9. The catalyst as claimed in claim 1 wherein Q is Si.

10. The catalyst as claimed in claim 1 wherein each $R^1$ is independently a $C_{1-8}$ hydrocarbyl or $C_{1-8}$ alkylamino.

11. The catalyst as claimed in claim 1 wherein each $R^2$ or $R^3$ is independently a $C_{1-20}$ hydrocarbyl, $C_{1-20}$ hydrocarbyl siloxy, $C_{1-20}$ hydrocarbyloxy or $C_{1-20}$ hydrocarbyl silyl group.

12. The catalyst as claimed in claim 11 wherein each $R^2$ or $R^3$ is independently a $C_{1-8}$ hydrocarbyl group or $C_{1-20}$ hydrocarbylsiloxy group attached to the ring via the oxygen atom.

13. The catalyst as claimed of claim 1 wherein $R^3$ is H.

14. The catalyst as claimed in claim 1 wherein a group L—Z is present at the 1 or 3 position of formula (IV).

15. The catalyst as claimed in claim 14 wherein L is $SiR^2{}_2$ or $(CR^2{}_2)_q$ in which q is 1 to 3 and $R_2$ is as hereinbefore defined.

16. The catalyst as claimed in claim 15 wherein L is $(CH_2)_q$ or $Si(CH_3)_2$.

17. The catalyst as claimed in claim 1 wherein at least one group —OQ$(R^1)_3$ is a siloxy or germyloxy group directly attached to the 4-position or 7-position.

18. The catalyst as claimed in claim 1 where a, b and c are 1.

19. The catalyst as claimed in claim 1 wherein at least two groups —OQ$(R^1)_3$ are present, one at position 4, one at position 7 of formula (IV).

20. The catalyst as claimed in claim 1 wherein $(R^1)_3QO$— is selected from the group consisting of $OSi(CH_3)_2$ $N(C_{1-6}$—alkyl)H,

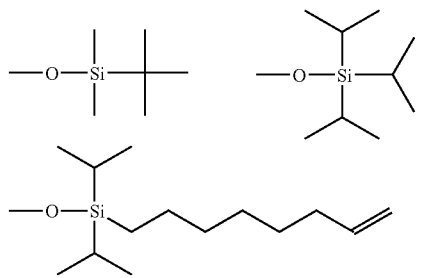

and

-continued

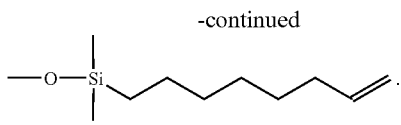
5

21. The catalyst as claimed in claim 1 wherein Z is present and both moieties of formula (IV) are identical.

22. The catalyst as claimed in claim 1 wherein Lig is of formula

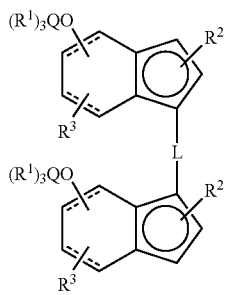

wherein $R^1$, $R^2$, $R^3$, Q and L are as hereinbefore defined.

23. An olefin polymerization catalyst system comprising or produced by the reaction of:
(i) a metallocene catalyst as claimed in claim 1; and
(ii) a cocatalyst/catalyst activator.

24. A process for olefin polymerization comprising polymerising an olefin in the presence of a metallocene catalyst as claimed in claim 1.

25. A process for the preparation of a metallocene catalyst as claimed in claim 1 which comprises metallating a $\eta^5$ cyclopentadienyl ligand which forms part of an indenyl or indenyloid moiety with a transition metal or a lanthanide.

26. A ligand of formula (IV)

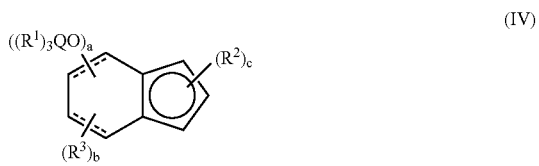

wherein one or more of the ring carbon atoms may be replaced by a ring heteroatom;
each Q is either a silicon or a germanium atom;
either or both of the bonds shown as ----- may be present or absent;
each $R^1$ which may be the same or different is a $C_{1-20}$ hydrocarbyl or a $C_{1-8}$ alkylamino at least one group $(R^1)_3QO$—being present on the 4 or 7 position;
each $R^2$ may be hydrogen or a group bonded to the 5-membered ring through a carbon, oxygen, silicon, germanium, nitrogen or sulfur;
each $R^3$ may be hydrogen or a group bonded to the 6-membered ring through a carbon, oxygen, silicon, germanium, nitrogen or sulfur; or
two or more $R^2$ and/or two or more $R^3$ groups attached to adjacent ring atoms on the same ring together form a 5- to 8-membered fused ring; and optionally
one $R^2$ or $R^3$ is —L—Z wherein L is a 1 to 4 atom chain and Z is a second moiety of formula (IV),
a is an integer between 1 and 3,
b is an integer between 1 and 3, the sum of a and b being no more than 4,
c is an integer between 1 and 3, with the proviso that no more than one —L—Z group is present and salts and complexes thereof.

* * * * *